United States Patent
Wolz

(10) Patent No.: US 10,500,021 B2
(45) Date of Patent: *Dec. 10, 2019

(54) PROCESS FOR PRODUCING A POLYCHROMIC AND/OR SPATIALLY POLYCHROMIC OR A MONOCHROME-COLORED CERAMIC BODY AND DEVICE FOR THIS PURPOSE

(71) Applicant: WDT-Wolz-Dental-Technik GmbH, Bad Sobernheim (DE)

(72) Inventor: Stefan Wolz, Bad Sobernheim (DE)

(73) Assignee: WDT-Wolz-Dental-Technik GmbH, Sobernheim (DE)

( * ) Notice: Subject to any disclaimer, the term of this patent is extended or adjusted under 35 U.S.C. 154(b) by 314 days.

This patent is subject to a terminal disclaimer.

(21) Appl. No.: 15/364,651

(22) Filed: Nov. 30, 2016

(65) Prior Publication Data
US 2017/0157645 A1    Jun. 8, 2017

(30) Foreign Application Priority Data

Dec. 7, 2015   (DE) .................. 10 2015 121 246
May 12, 2016   (EP) .................................. 16169366

(51) Int. Cl.
*A61C 13/00*   (2006.01)
*A61C 13/08*   (2006.01)
(Continued)

(52) U.S. Cl.
CPC ........ *A61C 13/0022* (2013.01); *A61C 8/0012* (2013.01); *A61C 8/0018* (2013.01); *A61C 13/0004* (2013.01); *A61C 13/0006* (2013.01); *A61C 13/082* (2013.01); *A61C 13/083* (2013.01); *A61C 13/20* (2013.01); *B05D 1/28* (2013.01); *B05D 3/007* (2013.01); *B05D 3/0254* (2013.01); *B05D 5/06* (2013.01); *B28B 11/243* (2013.01); *C03C 19/00* (2013.01); *C03C 23/0095* (2013.01); *A61C 8/005* (2013.01); *A61C 13/001* (2013.01); *A61L 27/047* (2013.01); *A61L 27/56* (2013.01)

(58) Field of Classification Search
CPC ............................ A61C 13/00; A61C 13/082
See application file for complete search history.

(56) References Cited

FOREIGN PATENT DOCUMENTS

WO   WO-2014206439 A1 * 12/2014 ........... C04B 41/009

OTHER PUBLICATIONS

Liu et al. Fabrication of coloured zirconia ceramics by infiltrating water debound injection moulded green body. Advances in Applied Ceramics . 2010 (Year: 2010).*

* cited by examiner

*Primary Examiner* — Cachet I Proctor
(74) *Attorney, Agent, or Firm* — Frank H. Foster; Kremblas & Foster

(57) ABSTRACT

A method for the production of a polychromatic and/or spatially polychromatic or a monochrome colored ceramic body, in particular a dentine ceramic blank, which is dyed in this way, wherein in order to control a targeted distribution of color pigments (101, 102) within a porous ceramic (100), in a first step, which is a loading step (3c), the ceramic (100) is loaded with a color pigment solution (104). In a second step, which is a distribution control step (4d), the distribution of the color pigments (101, 102) within the ceramic (100) is controlled by controlling one or more environmental parameters (106) in an environment (108) and/or the pressure and/or temperature.

14 Claims, 9 Drawing Sheets

Figure 1:
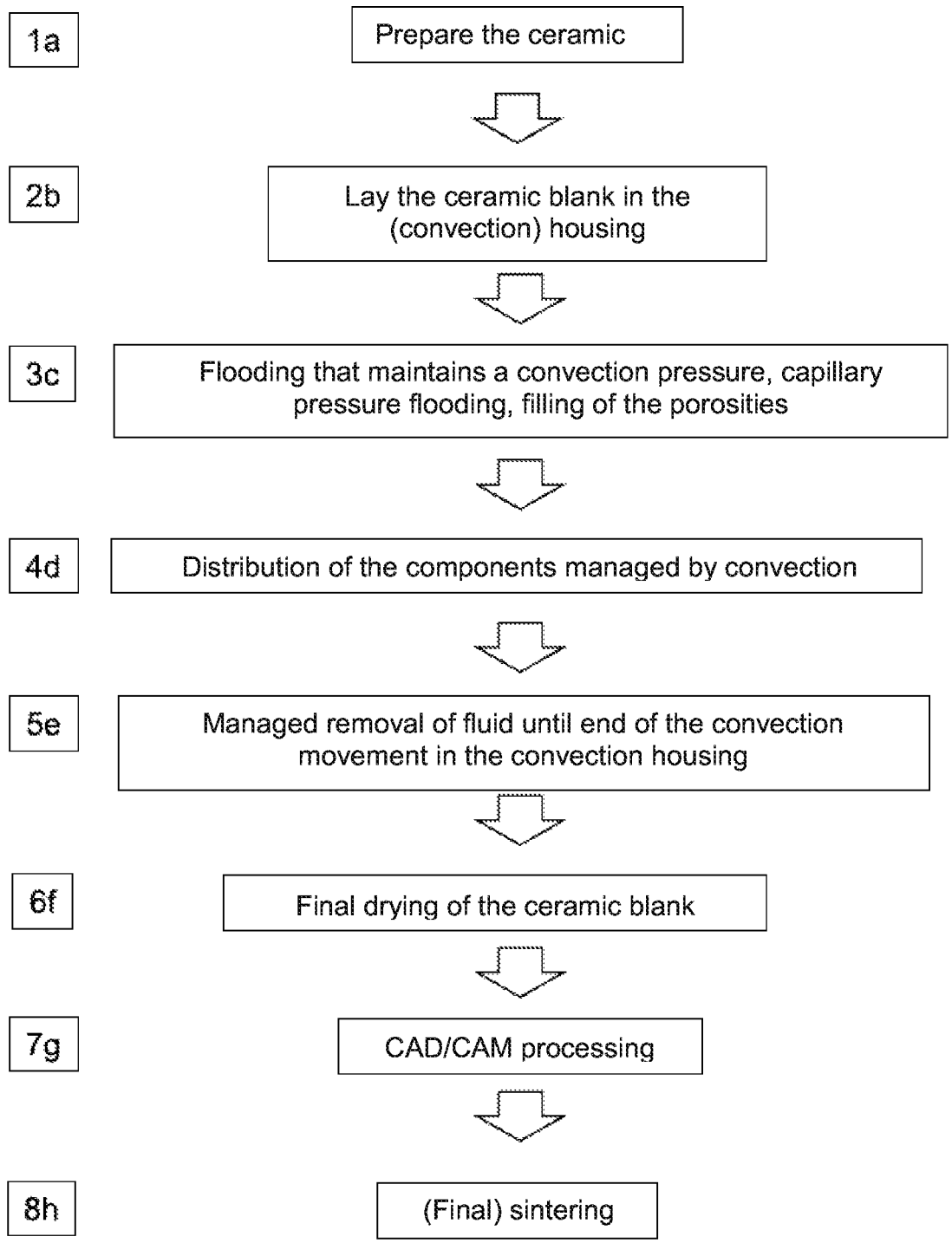

(51) Int. Cl.
*A61C 13/083* (2006.01)
*B05D 1/28* (2006.01)
*B05D 3/02* (2006.01)
*B05D 5/06* (2006.01)
*A61C 8/00* (2006.01)
*A61C 13/20* (2006.01)
*B05D 3/00* (2006.01)
*B28B 11/24* (2006.01)
*C03C 19/00* (2006.01)
*C03C 23/00* (2006.01)
*A61L 27/04* (2006.01)
*A61L 27/56* (2006.01)

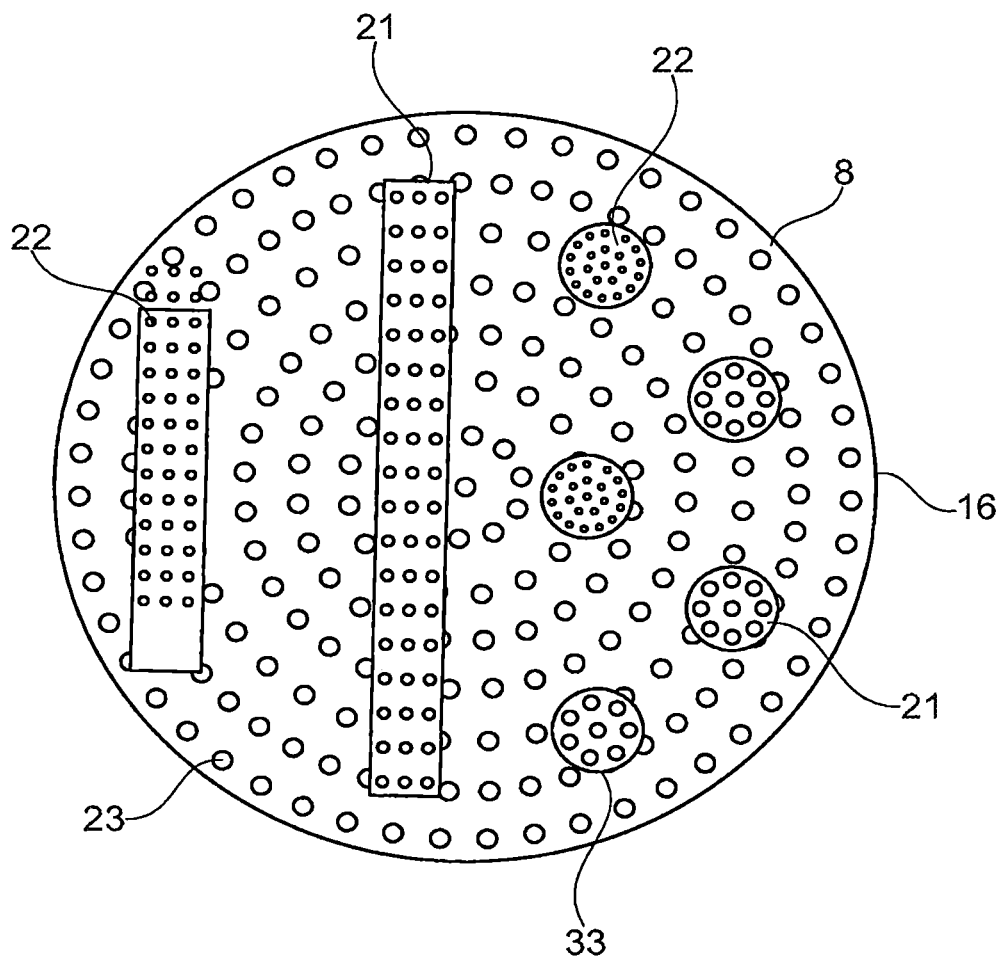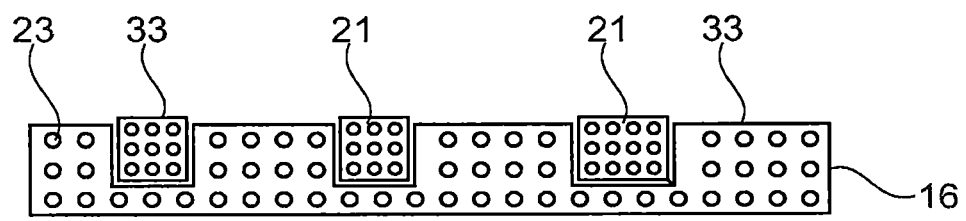
Fig. 8

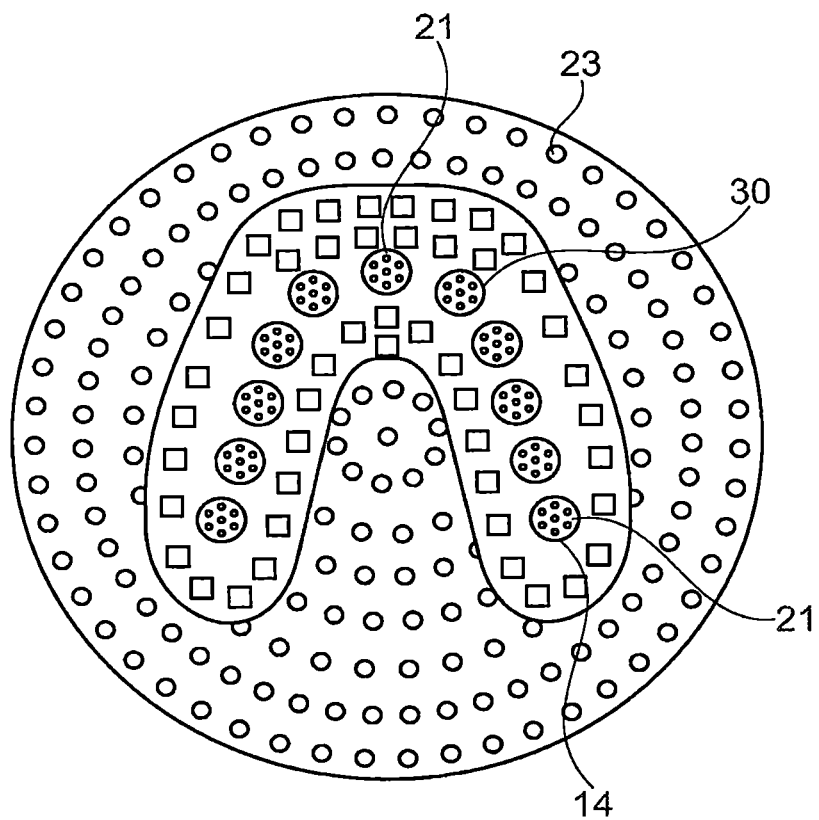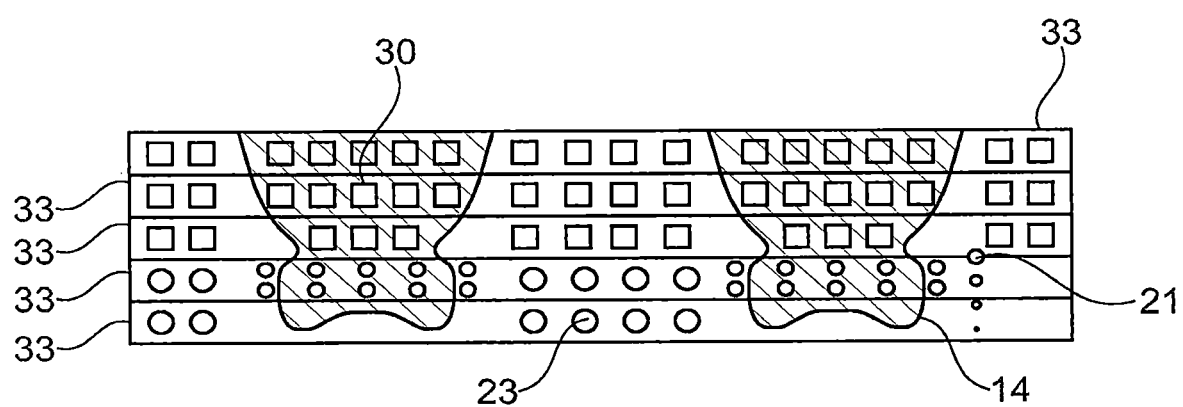
Fig. 9

PROCESS FOR PRODUCING A POLYCHROMIC AND/OR SPATIALLY POLYCHROMIC OR A MONOCHROME-COLORED CERAMIC BODY AND DEVICE FOR THIS PURPOSE

BACKGROUND OF THE INVENTION

The invention relates to a method for manufacturing a polychromic and/or spatially polychromic or a monochrome colored ceramic body, whereby a monochrome colored body essentially is of one color, a polychromic colored body has a two-dimensional color scheme, and a spatially colored polychromic has any desired color schemes or color distributions in any desired spatially directions. In particular the invention relates to a procedure for manufacturing a colored dental ceramic blank of a type that is suitable for processing by CAD/CAM.

Recently the use of hydrostabilized zircon has become thoroughly implemented in dental technology in the area of full ceramics. The major reason for this is the high stability of the high-performance ceramic frame. The final application of color occurs in a full ceramic tooth replacement by applying an additional ceramic coat on the tooth replacement already milled to a form, such as crowns or bridges. The additional ceramic coat today is still very expensive, and every individual tooth replacement has to be applied individually by hand. A machine manufacture is not possible. Still, as proven by studies, aesthetic blended ceramics manufactured in this way that have excellent color coats and shaping possibilities have a five times greater burst rate than the tried and tested blended metal ceramics (VMK). Because of frequent claims and high manufacturing costs, aesthetic blended ceramics should be rejected. Without the possibilities for adding color that blended ceramics has, only one tooth replacement can be manufactured, which essentially has no aesthetics.

According to DE11 2009 001 253 WO 2008 098 157, WO 2013 055 432, WO 0046 168, WO 2004 110 959, DE 199 04 522 B4, DE 10 2008 026 980 A1, WO 00/46168 A1, WO 2011/156602 A2 and DE 20 2011 109 956 U1, WO 11 15 66 02, EP 2013 06 31 20, metal ion solutions and/or metal complex solutions and gels for coloring porous dental ceramics have been developed, which imitate the current single color basic body of a tooth. However, one should note that no single color tooth exists in the mouth of a patient. This is also explained in DE 10 2008 026 980 A1. On the corners of a tooth, such as on a cutting edge, color pigments accumulate, whereby these corners appear darker than the rest of the tooth. In a natural tooth, the color related darker dentine core is covered over by an ever thicker cutting edge material down to a transparent tooth cutting edge.

To the greatest extent possible, a simple and single color coloration is achieved by immersion or spraying of the replacement tooth. To be sure, the attempt is made using a brush or applications by drops to achieve tooth coloring structures or similar colorings on the replacement tooth, but with the known fluids, solutions, or gels no result identical to nature can be achieved, so that as a result there are significant color differences between natural teeth and a replacement tooth. In addition, it is known from DE 199 04 522 B4 that regardless of the application duration of the fluid or the solution or the gel from 2 minutes to 20 minutes, the same color tone is always achieved. The depth of the effect is also decisive for color development, particularly in the transition to another color. All teachings have shown that specific drying processes with long-term effects must be performed by dental technicians.

Another disadvantage of fluids or solutions results from the fact that drops cannot be applied according to the individual situation and are therefore uncontrollably distributed over the completely porous ceramic. For example, it is not possible to color only the crown edges or only the crown tips, since the color dispensing drops run straight to the corners or tips. Furthermore, with the application instruments, such as marking pens and brushes, air is coated in, or air that is already existing within the porous ceramic replacement tooth is completely sucked in when the porous ceramic is completely immersed, and as a result the enclosed air can cause there to be no filling of the porosities and subsequently lead to no coloring of the ceramic.

A brush used for applying the color has for example an uncontrollable supply of coloring fluid and/or color removing solutions and/or color removing materials and gels. Consequently there is a principle of chance as to how much coloring and/or color removing material is taken up by the brush. A drop too much can also not be avoided or corrected. Should this occur, the complete tooth replacement must be newly prepared or manufactured. All teachings include only the failure of color dispensing components or removal of color dispensing components.

The solutions and gels that are composed on a water or alcohol basis lie at the base of rapid evaporation. The evaporation, which for example arises through incorrect storage, increases the concentration of solutions and gels so that as a result the color tone is changed in an undesired fashion. Moreover, solutions or fluids or gels leave behind drops and run out, and thereby there is contamination, evaporation, and adhesion. That is why wearing protective clothing, protective gloves, and protective spectacles is the rule.

That is why if a crown or the tooth replacement has an aesthetic result, the characteristics that subsequently occur should be considered and implemented. For one thing, the dentine coating must have the basic tooth color of the patient. The dentine color and the strength of the cutting coating form the particular tooth color of the patient. The natural tooth while growing or through later wear and tear forms the three-dimensional color combination. Otherwise there is also an ever brighter color scheme from the dentine core all the way to the cutting edge. The tooth enamel can also partially show bright and/or transparent spots. In addition, in older patients, the dark dentine color crown edges are quite visible, and as a result the new tooth replacement must be adjusted accordingly. If the tooth replacement is not individualized manually, but manufactured automatically, for example a multiplicity of quite different ceramic blanks must be manufactured in order to achieve cost reductions and aesthetic results.

In a situation that differs from the previously described manufacturing methods, it is not the milled out tooth replacement or the porous tooth replacement frame that is colored, but the initial material for manufacture of the ceramic blank is colored, for example the ceramic powder or ceramic paste.

This solution is proposed by EP 202 4300, WO 2014 062 375, WO 02 09 6 12, U.S. Pat. No. 9,212,065 B2, DE 2020 090 187 24, EP 235 97 71 and EP 185 97 57. These teach the covering of the initial material, in particular of powders and pastes. The powder or pastes are poured on or applied, whereby each coating has a concrete color. In this way 7-10 coatings are necessary to achieve a two-dimensional color application or a two-dimensional color scheme. DE 2020

090 187 24, U.S. Pat. No. 9,119,696, WO 02 09 6 12 teach that these coatings are curved, meaning that other costs arise for special tools as well as for an expensive multi-powder application with a precise dose application distribution. In addition, manufacturing according to these teachings is limited to individual crowns. Moreover, EP 18 59 75 7 shows the difficulties that arise in the transitions from coating to color coating. It teaches that a coating in the transition zone should be laid out with intermediate coatings. With 7-10 coatings multiplied by the 16 basic tooth colors, hundreds of powder and paste mixing possibilities result, which in each case are associated with high costs, hundreds of batch test and monitoring costs, and enormous storage costs. The blanks are still sintered on. Since the baking ovens on quality grounds can bake only one tooth color, there are further increases in the energy costs. A color scheme within a color coating from inside to the outside, and thereby a three-dimensional colors scheme identical to nature, cannot be achieved with the manufacturing methods described here.

It is therefore the task of the invention to provide an inexpensive alternative manufacturing method for a monochrome, polychromic, and/or spatially polychromic colored ceramic body and an device for such manufacture.

For the solution, reference is made to a method according to claim 1.

SUMMARY OF THE INVENTION

The inventive method is characterized that by controlling a targeted distribution of color pigments in a first step, which is a loading step, the porous ceramic can be loaded with a color pigment solution. In general a loading is to be understood as the introduction of color pigments into the porous ceramic, preferentially to a surface of the porous ceramic. The loading can in particular occur through applying color pigments, preferentially a color pigment solution, with a brush or a similar appropriate application pool, but also by spraying the porous ceramic with a color pigment solution or by simple immersion of the porous ceramic in a color pigment solution. What is meant by a porous ceramic, in particular in dental technology, is in general a porous ceramic body that for example is formed by pressing out the ceramic powder or pouring slip made of ceramic slip or through similar, appropriate methods. In order to rationally distribute color pigments, for example, metallic ions or metal oxide, or other organic or inorganic color pigments within the porous ceramic, these products must be contained in a fluid color pigment solution, in particular an aqueous one. In a second step that is a distribution control step, the distribution of the color pigments is managed within the porous ceramic. That means that the movement of the color pigments is controlled in such a way that they are transported to any desired positions within the porous ceramic. For this purpose, one or several environmental parameters are regulated, in particular the air humidity and/or the pressure and/or the temperature in an environment, for example a closed vessel, cupboard, room, or similar place in which the porous ceramic is located. With control that is not exclusively quantitative, but a control that is understood to relate to specific local areas within the environment, this means that the porous ceramic can be applied to various surfaces and/or surface areas with one or more environmental parameters.

In an advantageous variant of the method, the distribution of the color pigments within the porous ceramic is effected by a convection flow. For this, a flow direction and velocity, preferentially of the color pigment solution, is controlled through specific creation of environmental parameter gradients within the environment. In particular, humidity differences and/or pressure differences and/or temperature differences are set with regard to various surfaces and/or various surface areas of the porous ceramic.

According to an advantageous embodiment of the method, a movement velocity of the color pigments and/or the streaming velocity, in particular the color pigment solution, is managed through raising and/or lowering one or more of the environmental parameter gradients. For example, an initial environmental pressure that lies on the first surface of the porous ceramic can be increased, and a second environmental pressure that lies on a second surface opposite the first surface of the porous ceramic can be reduced or held constant, whereby the pressure gradient relative to both surfaces is increased. This then leads to a change, in particular to an increase of the movement velocity and/or the flow velocity.

According to such an advantageous embodiment of the method, a movement direction of the color pigments and/or the streaming direction, in particular the color pigment solution, is controlled by changing the direction of one or more of the environmental parameter gradients. For example, the first environmental pressure can be laid on a first surface of the porous ceramic, and the second environmental pressure can be laid on a third surface of the porous ceramic, whereby the movement direction and/or a streaming direction can lead to a color scheme change between the first and third surface of the porous ceramic. Through a reversal of the environmental parameter gradient color scheme (meaning a change of the mathematical sign of the gradient), the movement direction and/or the flow direction for example between the first and second surface can be reversed.

In an optional method variant, at least one surface or at least one part of a surface of the porous ceramic is insulated and/or reduced in thickness opposite the environment during the loading step and/or during the distribution control step. At least one other surface or at least one other part of a surface of the porous ceramic is freely accessible to loading and/or control, meaning that it is connected with the environment. In this manner the environmental parameters can be regulated in a specific position with regard to defined surfaces and/or partial surface areas. The insulation and/or sealing can be applied during the loading step for local targeted loading of the porous ceramic with the color pigments or the color pigment solution and/or during the distribution control step for targeted distribution, in particular for targeted controlling of the movement direction and/or the streaming direction.

The loading of the porous ceramic occurs advantageously with the color pigments, in particular with the color pigment solution, over the at least one freely accessible surface.

According to an optional variant of the method, the freely accessible surfaces of the porous ceramic are insulated and/or sealed before loading with the color pigments and/or with the color pigment solution, so that as a result parts of these surfaces or surface areas are inaccessible for loading with the color pigments or the color pigment solution and/or for the application of environmental parameters. Advantageously the freely accessible surface for loading with the color pigments and/or with the color pigment solution is directed downwards, pulled in the direction of gravity.

Optionally the at least one freely accessible surface of the porous ceramic may be connected with the environment during the distribution control step. The freely accessible surface in this manner can have applied one or several of the environmental parameters. Also, during the distribution control step the at least one insulated and/or sealed surface can be sealed and/or insulated against one or more of the environmental parameters. In this manner individual areas of the porous ceramic can be targeted to have environmental parameters applied, so that as a result the direction and degree of shape of the environmental parameter gradients can be regulated in targeted fashion in order to control the spatially distribution of the color pigments within the porous ceramic. Advantageously there is sealing and/or isolation by means of a form, a housing, or something similar and/or a foil and/or a coating. For example, the form can be a silicon form; the foil can be a self-adhesive foil, and the coating may involve a silicon, latex, and/or wax coating.

In an exemplary variant of the method, the porous ceramic for sealing and/or coating is applied tightly in a form, in particular a partially open silicon form, whereby the pressure within the form is less than for example the environmental pressure. In an example of an embodiment of the method, at least one first surface and/or at least one first partial surface area of the porous ceramic is set within the form, whereby this first surface and/or this first partial surface area is insulated and/or sealed against one environmental parameter, for example against humidity or the pressure that are present in the environment. At least one second surface and/or a second partial surface area is set outside the form, whereby the second surface and/or the second partial surface area is freely accessible relative to the environmental parameters. At least one third surface and/or a third partial surface area is set within the form and lies on an inner wall of the form, so that as a result within the form for example low pressure and/or high pressure can be set relative to the environmental pressure. For example, a pressure difference between the internal first surface and the external second surface of the porous ceramic can be set, in which the pressure within the form is lower than the environmental pressure. To reverse the direction of the pressure gradients, the pressure within the form can be increased or alternatively the environmental pressure can be decreased until the pressure within the form is higher than the environmental pressure lying on the second freely accessible surface. Alternatively, the porous ceramic within the form can be so set up that the first surface is set freely accessible outside the form, and the second surface is set to be insulated and/or sealed within the form. Optionally, the porous ceramic can be provided with additional environmental parameter gradients, such as humidity differences, whereby the humidity preferentially is regulated on the second freely accessible surface. Through the use of self-adhesive foil on the second freely accessible surface, an environmental parameter, such as the humidity, can be regulated with regard to individual second partial surface areas.

Advantageously the solution of the color pigment solution contains water and zircon nitrate. The intensity and/or the saturation of the individual colors or the color gradient can be controlled by the amount received of the added zircon nitrate or the amount of zircon nitrate in the color pigment solution.

Optionally, the loading of the porous ceramic can occur with the color pigments or with the color pigment solution using a loading body. In particular the loading body comprises a porous and/or spongy material, which facilitates the receipt of the color pigments or the color pigment solution into the color pigments contained there. The loading body is hereby mixed, in particular saturated, by a loading means and the color pigments contained in it. Preferentially for loading with the color pigments or the color pigment solution during the loading step, the porous ceramic is laid with a freely accessible surface on the loading body. The optional loading method offers the advantage that the total freely accessible surface of the porous ceramic is in moving contact with the loading body, whereby it is equally applied with color pigments. The number of color pigments and/or the color pigment concentration per surface that is applied to the porous ceramic during the loading step in this way can be held constant over the entire freely accessible surface.

The loading body can for example comprise one or several layers in which the one or the several layers contain identical color pigments for manufacture of a monochrome ceramic. A monochrome ceramic or a monochrome colored ceramic body can be manufactured in that for example all coatings layers of the loading body may be mixed and/or saturated with same color pigments, that is, mixed and/or saturated with the same color. In order to manufacture a polychromic ceramic or a polychromic colored ceramic body, various layers may be mixed and/or saturated with various color pigments, that is, mixed and/or saturated with various colors. The various layers of the loading body may be arranged horizontally next to one another and/or vertically under one another or over one another. By means of arranged layers even during the loading a vertical, polychromic color scheme within the ceramic body is facilitated or created. The porous ceramic to be loaded always stands connected to the uppermost layer of the loading body or lies on the uppermost layer of the loading body. The color pigments that are contained in the other layers run through the layers that are arranged above in each case before they penetrate into the porous ceramic. In this way a timely mixed loading with various color pigments is achieved, resulting in an unobtrusive color scheme. Even during the loading of the porous ceramic, a horizontal arrangement of the layers can facilitate or create a horizontal, polychromic color scheme inside the ceramic body. The porous ceramic to be loaded hereby is connected with all layers arranged horizontally next to one another, and lies on these so that the color pigments of the individual layers penetrate simultaneously the freely accessible surface on the porous ceramic, though at different partial surface areas. A combination of layers arranged vertically above or below one another and horizontally next to one another facilitates or creates even during loading a three-dimensional or spatially polychromic color scheme within the ceramic body. Depending on the desired final result, the combination of layers can occur horizontally next to one another and vertically over or above one another.

Naturally various color pigments for the manufacture of a polychromic or spatially polychromic colored ceramic body can also be inserted one after another in several loading steps, in each case with a single coating of the loading body of the porous ceramic.

According to one optional variant of the method, the loading body comprises a filter. The use of the filter of the in particular material acts equally or similarly to the other layers of the loading body, thus making it possible to achieve an equal distribution of the color pigments can during the loading step and thereby achieving a simpler control of the color scheme. In particular the filter contains a solution mixed with zircon nitrate.

Advantageously a drying of the porous ceramic occurs, in particular complete drying, even during the distribution management step. For example, the environmental parameters, in particular the humidity and/or the pressure and/or the temperature, can be regulated for controlling the drying process, whereby the drying time on one hand and the local course of drying on the other can be varied as desired. Thus drying in particular can occur of one, several, or all freely accessible surfaces of the porous ceramic or of the ceramic body. In particular the color pigments can be fixed at the desired position by drying, that is, through evaporation of the solution directly on the spot within the porous ceramic.

Alternatively or optionally the porous ceramic or the ceramic blank can be handled by heat in an additional drying step, which is connected to the distribution management step or to the distribution of the color pigments within the porous ceramic. The porous ceramic or the ceramic blank is hereby exposed for formation of an oxide phase, in particular a nitrate oxide phase with a temperature in the range between 80° C. and 1200° C., preferentially between 80° C. and 800° C. With oxygen, the cations in the solution, for example salts, in particular metallic salts that are included in the solution as color pigments, form an oxide or an oxide phase. In particular the porous ceramic body is handled with heat in order to achieve both the fixation of the color pigments and their development. In this way a dissolved metallic cation is formed with oxygen in metal oxide, what is called a metal oxide pigment, which conditions the coloring of the ceramic. By adding the zircon nitrate to the solution or to the color pigment solution and through a drying step with heat handling, the color pigments can be reliably fixed in the desired position. On the basis of the heat handling, the zircon nitrate forms a set structure within the pores of the porous ceramic, which encloses or fixes the color pigments. Heat handling allows in particular milling with water cooling CAD/CAM machines without fearing delocalization or shifting of the pigments within the porous ceramic.

During and/or after the distribution of the color pigments within the porous ceramic, according to an optional variant of the method a heat extension coefficient [WAK] balancing may take place, whereby the porous ceramic is loaded at least partially with a balancing material. To complete a tooth replacement, the ceramic blank ordinarily is subjected to final sintering, that is, high temperature handling, whereby a compression of the material is achieved and the porous spaces are filled up. On the basis of different heating extension coefficients [WAK] of the various materials, for example of the ceramic blank and the infiltrated color pigments, stresses may occur through volume expansions caused by the heat that differ from one another. Such stresses often lead to the formation of cracks, whereby the ceramic body becomes unusable as a tooth replacement. Through the addition of a balancing material, the various WAK values are balanced and stresses and cracking are avoided.

According to an exemplary inventive run of the method, in a first step a flat and/or plate shaped porous ceramic blank is prepared, in particular for use in the dental area. Plateform dental ceramic blanks are available commercially, and are suitable for processing with a standard CAD/CAM ceramic milling machine and the subsequent final sintering for manufacturing the tooth replacement. In a second step of the method, one or several surfaces of the ceramic blank are provided with insulation and/or sealing, whereby the ceramic blank is placed in a watertight and airtight sealed form, in particular a silicon form. Hereby at least one surface or one surface area of the ceramic blank is not insulated and/or sealed from the form, so that as a result this surface is freely accessible for manipulating with environmental parameters or for loading. In a third step, a loading step, the freely accessible surface or the freely accessible surface area of the ceramic blank is loaded with color pigments, whereby the color pigments, for example metallic salts, are contained in a liquid solution, in particular an aqueous one, or are present in a solution. In a fourth step, the ceramic blank is placed in an environment whose environmental parameters are adjustable, in particular the humidity and/or the pressure and/or the temperature. Hereby for example a climate cupboard or a drying cupboard may be involved, but even an accessible space, with the adjustable environmental parameters. In this way the ceramic blank can be retained in the form, so that only the freely accessible surface is connected with the environment. In a fifth step, a distribution management step, the distribution of the color pigments that are applied through the loading with the color pigment solution into the ceramic blank is managed within the ceramic blank. For this purpose, at least one environmental parameter for the creation of an environmental parameter gradient, in particular the humidity and/or the pressure and/or the temperature, is adjusted between the one or the several freely accessible surfaces and the one or the several insulated and/or sealed surfaces of the ceramic blank.

In an optional additional step of the method, the porous ceramic or the ceramic blank can be milled into the desired form after distribution and if necessary after the fixing of the color pigments using a CAD/CAM milling machine, in particular milled into the form of a part of a tooth replacement. In another optional additional step of the method, the porous ceramic or the ceramic blank can be for example milled, sintered, and/or end sintered after the distribution and if necessary after the fixing of the color pigments, and preferentially after processing into a form. In particular the ceramic blank may sintered on before the distribution of the color pigments at a lower temperature and after the distribution of the color pigments end sintered at a higher temperature.

The task of the invention is also solved by a ceramic blank that is suitable for manufacture of a tooth replacement by a CAD/CAM milling machine, and in particular manufactured according to the inventive method. The ceramic blank has a color pigment distribution that is controlled by environmental parameter gradients, whereby the ceramic blank has an equal monochrome coloring and/or a polychromic color scheme and/or a spatially polychromic color scheme.

An inventive device for loading a porous ceramic, in particular a dental ceramic blank with an aqueous color pigment solution, is so characterized that the loading device comprises a porous and/or spongy material. The porous and/or spongy material is mixable with the color pigment solution, preferentially available for satiation, so that it can be transferred to the for example laid down porous ceramic, or the porous ceramic can be loaded with it. According to an advantageous embodiment, the loading device comprises at least two layers, whereby at least one layer is set up as a filter, that is, not mixed with color pigments, and/or at least two layers are mixed with different color pigments in each case.

An inventive device for managing a desired distribution of color pigments within a porous ceramic, in particular a dental ceramic blank, is suitable for insulation and/or sealing of at least one surface and/or least one part of a surface of the porous ceramic, whereby at least one other surface and/or at least one other part of a surface is freely accessible for application of adjustable environmental parameters. For example, the device involves an opened form, in particular a silicon form, which is set up for tightly fitting acceptance of the porous ceramic, so that the porous ceramic is accepted in final form by the silicon form, whereby a surface of the porous ceramic is freely accessible.

Further exemplary characteristics, combinations of characteristics, and formations as part of the invention may be found in the following sections.

As a rule, the corresponding solutions can be manufactured simply in a way that a corresponding for example metal salt is dissolved in the corresponding solutions, preferentially water.

Preferentially the invention begins from the corresponding salts, such as chlorates, sulfates, carbonates, or in particular nitrates of the for example particular metal. The rare-earth elements also specifically include in particular the lanthanide groups. Among the supplementary group elements, in particular one should emphasize the transitional metals and supplementary groups 1-8, main group I-VIII, based on the latest nomenclature of the periodic table.

The expression that is used, "solution", is known to the person skilled in the art without further explanation, and should here be understood as widely as possible. Obviously the metal ions and the metal complexes are prepared inventively in a form in which they can most easily penetrate into the porous ceramic material. Therefore as a rule here a (liquid) solution or a homogeneous mixture of corresponding solids in the solution are to be loaded into the porosities of the ceramic body. After the drying of the nitrates in the porosities, a crystal develops that can also run through an oxidation stage by separate heat handling.

In the inventive method, suspensions are especially preferred for use, in particular solutions that contain metal ions of the metal complexes with at least one element of the listed elements.

1. $Fe(No_3)_3 \cdot 9H_2O$
2. $Cr((No_3)_3 \cdot 9H_2O$
3. $Er(No_3)_3 \cdot 5H_2O$
4. $Ce(No_3)_3 \cdot 6H_2O$
5. $Al(No_3)_3 \cdot 9H_2O$
6. $Ni(No_3)_2 \cdot 6H_2O$
7. $Mn(No_3) \cdot 4H_2O$
8. $Pr(No_3)_3 \cdot 6H_2O$
9. $Y(No_3)_3 \cdot 6H_2O$
10. $Co(No_3)_2 \cdot 6H_2O$
11. $ZrO(No_3)_2 \cdot xH_2O$
12. $Sm(No_3)_3 \cdot 6H_2O$
13. $Nd(No_3)_3 \cdot 6H_2O$
14. $Eu(No_3)_3 \cdot 5H_2O$
15. $Dy(No_3)_3 \cdot xH_2O$
16. $Yb(No_3)_3 \cdot 5H_2O$
17. $Ti(No_3)_4 \cdot 4H_2O$
18. $Bi(No_3)_3 \cdot 5H_2O$
19. AuCi
20. $Sr(No_3)_2$
21. $Mg(No_3)_2 \cdot 6H_2O$
22. $La(No_3)_3 \cdot 6H_2O$
23. $Ag\ No_3$.
24. $In(No_3)_3 \cdot XH_2O$
25. $Cd(No_3)_2 \cdot 4H_2O$
26. $V(No_3)$
27. $Zn(No_3)_2 \cdot 6H_2O$
28. $Dy(No_3)_3 \cdot xH_2O$
29. $Tb(No_3)_3 \cdot 5H_2O$
30. $Ca(No_3)_2 \cdot xH_2O$
31. $C_4H_4NNbo_9 \cdot xH_2O$
32. $Pb(No_3)_2$
33. $Nb(No_3)_3 \cdot 5H_2O$
34. $Hf(No_3)_4$
35. $Zr\ (So_4)_2 \cdot H_2O$ In the proposed method for coloring bound and/or unbound and/or sintered on and/or completely porous ceramics, in particular ceramic bodies that are applied in dental technology, the color dispensing distribution in ceramic bodies and/or also in ready to market ceramic blanks occurs in a sealed housing, for example of silicon, in order to control the movement direction of the color pigments. In the for example silicon housing, there is also a space with and/or without spherical pressure with and/or loading body materials for continuous air-free filling of the porosities. By sealing and/or insulation means of a form, one understands all materials that may surround the surfaces of a porous ceramic blank in a sealed fashion and/or in a fashion that permits air to pass through. Preferentially, a surface of the porous ceramic blank is placed on a solution device with loading body materials that maintain capillary pressure, in which or on which the color pigment solutions are stored. Preferentially the attachment of loading body materials should be manufactured for air-free transport, such as microfibers, sponges, pulp, etc. Under the concept loading body material, one understands all materials or raw materials that allow water to pass through and/or that can store these materials. The loading body materials fulfill an important purpose. The capillary pressure of the porous ceramic is so strong that for example our tongue adheres immediately to the porous ceramic. This depends on the very high density of the porous ceramic. If the porous ceramic is applied with a brush or with fluids, these are immediately vacuumed away, but the color dispensing components are slower than the solution liquid. Thus the porous ceramic acts as a filter in which the color dispensing components can then be concentrated somewhere in accumulated fashion. The distribution management step can dissolve these and distribute them again in this ceramic block. However, this can mean several days in the for example silicon housing with the corresponding environmental parameters. Basically, a loading body material is sought that has the effect of holding back the fluid, depending on the porosity of the ceramic blank. In this way there are essentially fewer undesired concentration clumps. The color dispensing components may then more quickly achieve a desired color dispensing distribution during the distribution management step. In addition, various color dispensing components can be set up in desired volumes in layers, meaning 50 ml total volume of the current ceramic porosities can be applied in each of the various loading body materials at 10 ml each. Through equal capillary pressure, now five various color component solutions can be laid over one another and stored without there being mixed, something that would otherwise be almost impossible in a fluid. Through the capillary pressure maintaining device for loading the body material, a capillary low-pressure loading occurs because a color dispensing solution passes the pressure further on to the others, and thereby basically different and/or running color transfers occur. The color pigment solution and/or loading body material may introduce with or without pressure the color dispensing components and/or fireproof pigments and/or oxides and/or coloring and fluorescent metal oxides and/or organic or inorganic salts with a color pigment solution. This means that the loading body material accepts the desired capillary pressure when there is a moist and/or wet foundation. The loading body materials then serve as color solution storage of color pigment solutions for complete loading of all porosities of the porous ceramic. By color dispensing components of the color pigment solutions, one understands all color dispensing and non-color dispensing components that lead to the desired ceramic blank that is stress free and capable of being sintered.

Inventively, the desired distribution management step of the color dispensing concentrations of organic or inorganic salts takes place for example in a manageable sealing material and/or insulating material for example of a form. Preferentially this can be manufactured from a for example silicon form. Surprisingly, it has been discovered that even in a porous ceramic that is located in a for example silicon housing the distribution management step takes place, which is similar to the convection of a fluid in a vessel. In the inventive procedure, all convections may be applied before a chemical convection. In a solution there may be a solutal convection in which a standing saline solution is applied, as well as haline convection, thermohaline convection, mahogany convection, and electric convection. The convection is exchanged through the properties of the material, form bodies, flows that are affected, energy, entropy, materials, and electrical loads that are exchanged through such means as diffusion, fiber transfers, drying, sorption, evaporation, solidification, disassociation, lissociation, and friction. In addition, a surface may act as a catalyst. For these reasons convection is also difficult to calculate. Through many hundreds of trials and even thousands of possibilities, a distribution management step has been found out that has precise color through haline convection and its settings. Convection due to gravitation and differences in density is also controlled for the amount of organic and inorganic salts, as well as by electrostatic fields with temperature differences and differences in the surrounding moisture content. This is the same in the creation of open or covered surface ends of the porous ceramic blank. The porous ceramic blank may be round, 10-50 mm high, or may have a diameter of 10-150 mm or a horseshoe form or correspond to the enlarged form of a total jaw, or may also have material saving forms and recesses.

For transport of the fluid of the manageable color pigment solution, inventively water or a mixture of water with an organic solution, in particular a polar organic solution, is used. The color dispensing components and/or fireproof pigments and/or oxides and/or coloring and fluorescent metal oxides and/or organic or inorganic salts contain an aqueous solution or alcohol distillate, and/or such a solution or distillate occurs. Organic solutions are for example aliphatic alcohols. The solution and/or transport fluid may if necessary contain additives, such as stabilizers or electrolytes, complex creators, dispersion materials, etc. The additives are contained either in the loading by the material or in the color pigment solution. By color pigment solution, one understands all solutions that are found in a porous ceramic in the porosities, and that are distributed in a managed fashion through open and closed surfaces onto the porous ceramic blank.

It is also expeditious that there are applied in the color pigment solution an oxidation material, aluminum nitrate, in particular hydrogen peroxide, and/or solid salts and/or zirconium (IV) oxynitrate hydrate. It is also expeditious that oils and/or benzene be applied in the color pigment solution. There is thus also a reduction of flow and a filter lying between the loading body material memory and the for example silicon housing. The capillary body is then a filter for reduction of flow, and initially takes care of the fact that there be the least possible concentration of clumps in the porous ceramic blank and secondarily thereby takes care of a low-pressure capillary loading. Since the applied surfaces of the porous ceramic are always contaminated with zircon dust, something that contaminates the color pigment solution, as are the loading body materials and/or capillary reduction of flow and filter and loading body material memory.

In a possible inventive variant of the method, the color pigment solutions and/or fireproof pigments and/or oxide and/or coloring and fluorescent metal oxides and/or organic or inorganic salts are loaded in or under a vacuum atmosphere in the convection housing. Transporting the color dispensing components and/or fireproof pigments and/or oxides and/or coloring and fluorescent metal oxides and/or organic or inorganic salts of the color pigment solutions can also take place under an approximate vacuum atmosphere. This is however not absolutely necessary. Depending on the porosity of the ceramic blank, too strong a vacuum may lead to unfilled porosities and/or to undesirable concentration clumps of the color dispensing components.

In a possible further inventive variant of the method, the color pigment solutions and/or fireproof pigments and/or oxide and/or coloring and fluorescent metal oxides and/or organic or inorganic salts of the haline convections are transported under pressure. Thereby the capillary pressure can also be increased through applying pressure with the loading material solution device that contains capillary pressure. Too much pressure can lead to excess application pressure or not enough application pressure on porosities and their hollow spaces; this may cause strong blockages and thereby lead to undesirable concentration clumps of the color dispensing components. The loading material solution device that contains capillary pressure is understood as all dense applications or acceptance pieces of device in which or on which solutions with color and non-color dispensing components can be stored with increase and/or reduction of the capillary pressure in the porosities of the ceramic.

In the inventive method, the color pigment solution with and/or fireproof pigments and/or oxides and/or coloring and fluorescent metal oxides and/or organic or inorganic salts are loaded into the pores of the porous ceramic with a loading body material using capillary pressure maintaining color solutions and/or applied under capillary low-pressure loading. Porous openings exist on the surface of the ceramic so that the color dispensing components and/or higher proof pigments and/or oxides and/or coloring and fluorescent metal oxides and/or organic or inorganic salts penetrate into these. The depth of the penetration depends on the amount of the color pigment solution and the regulated capillary pressure and the capillary pressure of the loading material solution device for maintaining capillary pressure. The loading material solution device for maintaining capillary pressure should be lower. All porosities are filled with color pigment solutions with the capillary pressure of the porous ceramic equally and not too quickly, without air inputs.

Expeditiously the loading body materials are filled with color dispensing components and used as storage for the loading body material solution; these serve as a simple storage of color mixtures or as a filter. For example, a beer mat may then contain the desired concentrations and color dispensing components of the tooth color. Moreover, it sets a capillary reduction of the loading body material solution used for maintaining the capillary pressure. Through the application of the beer mat on the porous surface of the porous ceramic blank found in the for example silicon housing for example silicon housing is now laid flat on the loading material solution device that maintains the capillary pressure. In this way the color pigment solution can now be loaded at any places desired on the porous ceramic block. Loading body materials are understood as all materials and products that allow fluid to flow through and/or can contain such materials for reduction of current and/or capillary pressure relative to the porous ceramic.

The inventive method also offers the possibility that the equal and/or concentrated distribution of the distribution streaming step is managed by the for example silicon housing content of nitrate, temperature, humidity, and with various large surfaces that are in contact with the environmental humidity. One should pay attention here that the surrounding humidity not drop below 30% at temperatures of about 25°. Otherwise the movement direction of the color pigments leads to a strong concentration of clumps, something that is rarely desirable. This observation is however dependent on the particular existing porosity of the ceramic body.

During the inventive method, it is advantageous if color measurements on natural teeth are recorded in a programmable memory so that the color of the natural teeth can be reproduced with the corresponding color pigment solutions. The tooth color of the natural teeth of the patient is thereby measured. Then the noted color data are recorded in a piece of software or in a programmable memory. The software or the programmable memory can calculate or reproduce the natural tooth color with color pigment solutions based on the color data. The color scheme is then graphically displayed by the CAD/CAM system.

In addition, it was surprisingly discovered that, due to coverings or non-adhesions of vertical zebra stripes under non-adhering zebra stripes of the porous ceramic in this ceramic block, a running spatially color concentration wave occurs, or, with open or circular non-adhesions, a spatially color concentration conical form. If one surrounds the desired fields with various high frames, a higher humidity is set in the frame itself, even though a constant humidity exists. The surfaces with a high frame and higher humidity form a vertically running higher spatially color concentration. Surfaces with a low frame and low humidity form a more color insensitive and lower spatially color concentration in the porous ceramic block.

A further possibility of the method of the invention is that a program controlled machine or device, in particular a CAD/CAM utility, seeks out the color concentration available in the existing concentration zone fields of the ceramic blanks, and from these performs the milling that corresponds to the tooth color of the natural teeth. Furthermore, the loading body material may be milled up to a desired color scheme figuration—see FIG. 8 and FIG. 9—or have the anatomy of the surface of a tooth replacement.

Moreover, the inventive color dispensing colors stored by the color measurement that was performed are stored on the program controlled machine or sent to the program controlled device. The previously noted color data of the natural teeth of the patient are sent to the program controlled machine or device so that as a result the machine applies one or several loading body materials, and these are laid in a for example silicon housing in order to manufacture the tooth color of the patient's natural teeth. A spectrophotometer is helpful for setting the desired colors. Hereby the L*–value brightness (100 complete reflection, 0: no reflection):
a*=red-green coloring value
   (+a*: red, −a: green)
b*=yellow-blue coloring value
   (+b: yellow, −b: blue)

The nitrate color materials for example 0.05-0.7% chromium oxide or 0.05-0.2% copper nitrate or chromium nitrate are to be added; the pressed article takes on a brown or green color. For a reddish pink color, 0.05-2% erbium nitrate may be added. For a yellow color, 1-2% cerium nitrate or 0.05-2% vanadium nitrate may be added. For a violet color, 0.5-2% neodymium or 0.05-0.3% cobalt nitrate may be added. For an orange-yellow color, 0.05-0.5% iron nitrate is added. A multiplicity of color materials may also be used together in order to set the L*a*b* values.

The nitrate element may in each case be added in a color stabilizing pre-solution, made up of 0.0001-60% zircon nitrate, adapted to the solid material of the ceramic.

Obviously the for example pre-sintered ceramic must have open porosity for loading, so that the color dispensing elements may be moved in a distribution managed step, with the parameters in the porosity controlled. Such (open) porosities lie between >3% and 90%, and especially preferred between 25% and 30%. The nitrates and the nitrate formulas supplied in the color stabilizing pre-solution contain 0.0001-30%, and preferred between 0.0001% and 3%, in order to be able to achieve for example a Vita classical color scale of 16 colors A1-D4, and for example the following combinations may be implemented.

1. $Er(No_3)_3.5H_2O$ +$Fe(No_3).9H_2O$ $Pr(No_3)_36H_2O$+
2. $Y(No_3)_3.6H_2O$+$Er(No_3)_3.5H_2O$ $FeNo_3).9H_2O$+$Al(No_3).9H_2O$
3. $Pr(No_3)_3.6H_2O$+$Fe(No_3).9H_2O$+,$Tb(No_3).5H_2O$+$Mn(No_3)2. 4H_2O$
or
$Pr(No_3)6H_2O$+$Tb(No_3).5H_2O$ $Fe(No_3)9H_2O$, $Cr(No_3)_3.9H_2O$

For more precise settings, the following must be added:
$Yb(No_3)_3.5H_2O$ $Er(No_3)$, $Dy(No_3)_3.XH_2O$ $Eu(No_3)_3.5H_2O$, $Nd(No_3)_3.6H_2O$, $V(No)_3 .H_2O$, $Ti(No_3)_4.4H_2O$
Add 4. $Y(No_3)_3.6H_2O$, $Er(No_3)_3.5H_2O$
   $Pr(No_3)_3.6H_2O$, $Fe(No_3).9H_2O$, $Zn(No_3)_2.6H_2O$
5. $Fe(No_3)_3.9H_2O$, $Cr(No_3)_3.9H_2O$, $Ni(No_3)_2.6H_2O$, $Mn(No_3)_2. 4H_2O$
6. $Fe(No_3)_3.9H_2O$, $Cr(No_3)_3.9H_2O$, $Mn(No_3).4H_2O$
7. $Fe(No_3)_3.9H_2O$, $Ni(No_3)_2.6H_2O$
8. $Fe(No_3)_3.9H_2O$, $Ni(No_3)_2.6H_2O$, $Mn(No_3).4H_2O$
9. $Fe(No_3)_3.9H_2O$, $Cr(No_3)_3.9H_2O$
10. $Er(No_3)_3.5H_2O$, $Fe(No_3)_3$, $Cr(No_3)_3.9H_2O$
11. $Ni(No_3)_2.6H_2O$, $Pr(No_3)_3.6H_2O$
12. $Fe(No_3)_3.9H_2O$
13. $Er(No_3)_3.5H_2O$, $Ni(No_3)_2.6H_2O$
14. $Fe(No_3)_3.9H_2O$, $Ni(No_3)_2.6H_2O$, $Cr(No_3)_3.9H_2O$
15. $Er(No_3)_3.5H_2O$, $Fe(No_3)_3.9H_2O$
16. $Fe(No_3)_3.5H_2O$, $Bi(No_3)_3.5H_2O$, $Ce(No_3).6H_2O$
17. $Er(No_3)_3.5H_2O$, $Pr(No_3)_3.6H_2O$, $Fe(No_3)_3.9H_2O$, $Zn(No_3)_2. 6H_2O$
18. $Fe(No_3)_3.5H_2O$, $Cr(No_3)_3.9H_2O$, $Al(No_3)_3.9H_2O$
19. $Sr (No_3)_2$, $La(No_3)_3.6H_2O$, $Ag(No_3)$, $Mg(No_3)_2.6H_2O$, $Fe(No_3)_3. 9H_2O$, $Y(No_3)_3.6H_2O$,
    $AuCl$, $Zn(No_3)_2.6H_2O$, $Eu (No_3)_3.5H_2O$
20. $Fe(No_3)_3.9H_2O$, $Al(No_3).9H_2O$, $Er(No_3)_3.5H_2O$
21. $Ce(No_3).6H_2O$, $Dy(No_3)_3.xH_2O$
22. $Pr(No_3)_3.6H_2O$, $Fe(No_3)_3.9H_2O$, $Tb(No_3)_3.5H_2O$
23. $Ce(No_3)_3.6H_2O$, $Y(No_3)_3.6H_2O$, $Al(No_3)_3.5H_2O$
24. $Ce(No_3)_3.6H_2O$, $Y(No_3)_3.6H_2O$, $Al(No_3)_3$, $Mn(No_3)_3. 4H_2O$, $Mg(No_3)_2.6H_2O$
25. $Ce(No_3)_3.6H_2O$, $Fe(No_3)_3.9H_2O$, $Al(No_3).9H_2O$, $Co(No_3)_2.6H_2O$
26. $Fe(No_3)_2. 9H2O$, $Cr(No_3)_3.9H_2O$, $Cu(No_3)_2.xH_2O$, $Y(No_3)_3.9H_2O$, $Pr(No_3)_3.6H_2O$,
    $Co(No_3)_2.6H_2O$, $Nr(No_3)_2.6H_2O$, $Mn(No_3)_2.4H_2O$, $Er(No_3)_2. 5H_2O$, $Ce(No_3)_3.6H_2O$ The characterization of the colors is done according to the CIE-L*a*b system of the International Commission (CIE), Vienna 1986. In this system, the Vita classical color ring of 16 colors involves the following range of values that are to be achieved and set.
L*50 to 76
a*-2.0 to 10.0
b*4.0 to 30.0
As possible, colors should be inventively concentrated but also measured:
L*2 to 50
a*-28.0 to 35.0
b*-15.0 to 31.0
As possible, the inventive transparent oxide ceramics and/or glass ceramics should be loaded, and the following values are to be achieved:
L*76 to 98
a*-4.2 to 28.0
b*-1.60 to 34.0

Surprisingly, it turned out that the color intensity can also be managed by the pre-solution, for example with zircon nitrate. This means that for comparison a sample 1.5 mm thick by 60 mm by 12 mm wide is visually equivalent to a sample that is 4.0 mm thick by 60 mm by 12 mm wide. In samples pressed with powdered oxide coloring in layering technology 1.5 mm thick by 65 mm by 12 mm wide, visually a much brighter color tone for the sample of 4.0 mm by 60 mm×12 mm wide. This has extreme effects on the aesthetics.

This means that the strength of the coating on the crown framework, approximately 0.5 mm to 1.5 mm, is much brighter than that of the missing teeth, meaning the bridge with a coating thickness of approximately 4-10 mm. The tooth technician can balance out this color difference only with significant intensive work. With the inventive method, the addition of the described various pre-solution concentrations sets giving color that is optically equivalent to the same color tone, for example 1.5 mm and 4.0 mm. For this, in each case 1.5 mm and 4.0 mm thick samples made of 3Y-TZP are held in a sintering program at 3° per minute at 1450° for 120 minutes, and cooled in the oven at 200°. The samples were measured with an SF 600* data color from the Warburg GmbH industrial paint factory. As a reference, a white background was selected with the following values:
L*94.94, a*3, 87, *-12.85
Sample pairs:
1. 3Y-TZP colored samples of powdered technical oxide
   4 mm=L*72.96 a*0.65 b*13.19
   1.5 mm=L*77.04 a*1.78 b*17.96
   gives a measurement difference range of 9.72
2. Pure 3Y-TZP from the same manufacturer with controlled color dispensing concentration of a 7% nitrate pre-solution with color dispensing nitrates
   4 mm=L*78.80 a*-0.24 b*17.80
   1.5 mm=L*78.32 a*-0.82 b*18.90
   gives a measurement difference range of 2.20
3. Out of caution, another sample of 3Y-TZP was manufactured, a color dispensing concentration of 7% nitrate pre-solution with color dispensing nitrates in a dark color tone (brownish)
   4 mm=L*49.90 a*3.41 b*9.37
   1.5 mm=L48.13 a*3.58 b*9.42
   gives a measurement difference range of 1.84
   Here too the 1.5 mm thick samples up to the different symbol for 4 mm thick samples could not be distinguished visually. A calculated improvement of the color constancy of approximately 70%.

In an advantageous variant of the method, the entire pre-sintered and/or pre-pressed ceramic blocks are colored before the CAD/CAM processing. This means that ceramic blocks can already be manufactured in various basic colors so that only the for example and/or the spatially color concentration conical form arise in the desired surfaces with a distribution controlled step or in order to balance a thermal extension of the WAK of the color dispensing oxides.

For an embodiment form of the method, a porous burned dental blended ceramic or a porous pressed glass ceramic is used as a ceramic. The method is applicable on all porous ceramics. It does not matter whether this involves pressed, burned, bound, unbound, and/or sintered ceramic. The ceramic must however have pores so that the color dispensing components and/or fireproof pigments and/or oxides and/or coloring and fluorescent metal oxides and/organic or inorganic salts permit at least a movement direction of the color pigments.

In the method, for example a porous ceramic comprises and uses the following: zircon oxide ($ZrO_2$), yttrium oxide ($Y_2O_3$), hafnium oxide ($HfO_7$), aluminum oxide ($Al_2O_3$), phosphorus oxide ($P_2O_3$, $P_2O_4$, $P_4O_{10}$), titanium oxide ($TiO_2$), tin oxide (SnO, $Sn_2O_3$, $SnO_2$), boron oxide (($BO)_x$, ($B_2O)_x$), boron oxide ($B_2O_3$), fluorine ($F_2$), sodium oxide ($Na_2O$), barium oxide (BaO), strontium oxide (SrO), strontium peroxide ($SrO_2$), magnesium oxide (MgO), zinc oxide (ZnO), tin oxide (SnO, $Sn_2O_3$, $SnO_2$), CaO (CaO), titanium oxide ($TiO_2$), niobium oxide (NbO, $NbO_2$, $Nb_2O_5$), tantalum oxide (TaO, $TaO_2$, $Ta_2O_5$), lanthanum oxide ($La_2O_3$), silicium oxide ($SiO_2$), lucite, vanadium(V)-oxide ($V_2O_5$), added spinels and/or other oxides and mixtures.

In addition in the inventive method, feldspar ceramics, zircon oxide ceramics, and/or leucite strengthened ceramics, lithium silicate glasses or lithium silicate glass ceramics or lithium disilicate glass ceramics, silicate ceramics, and/or oxide ceramics are colored. Any oxide ceramic or a ceramic based on oxide ceramics may be used for the method of coloring ceramics. Oxide ceramics are high-performance ceramics that are harder, more resistant to wear, more able to withstand heat, and more rigid than hard metals. Accordingly they offer the most important properties for an implant prosthesis or an implant and/or a tooth replacement. In addition, a ceramic that exists on the basis of glass ceramics and/or glass can be used.

In an inventive step of the method, the color dispensing components in the porous ceramic blanks are sintered in a rising vacuum atmosphere or in an oxygen-free or almost oxygen-free room in order to fix in the ceramic the color dispensing components and/or the fireproof pigments and/or oxides and/or coloring and fluorescent metal oxides and/or organic or inorganic salts. This means that the color dispensing components and/or fireproof pigments and/or oxides and/or coloring and fluorescent metal oxides and/or organic or inorganic salts are fixed in the pores of the ceramic by a sintering procedure, and/or are changed into an oxide in the desintering procedure.

The inventive method comprises the following steps:
(1) Preparation of a completely porous and/or pre-sintered and/or unbound and/or bound ceramic, in particular a ceramic body for the CAD/CAM processing
(2) Sealing and/or insulating using a form of the ceramic body
(3) Loading of the porosities of the ceramic body
(4) Distribution management step of the color dispensing elements
(5) Fluid removal up until the end of the management of the distribution in the sealed and/or insulated ceramic bodies
(6) Drying of the ceramic blank for crystal formation and/or heat handling during the oxide phase formation (7) CAD/CAM processing
(8) Final sintering and/or sintering for fixation in the oxide In the inventive color pigment solution, the following concentrations are contained: between 0.001% and 60%, or preferentially between 0.0001% and 3%, of the color dispensing components and/or fireproof pigments and/or oxides and/or coloring and fluorescent metal oxides and/or organic or inorganic salts. According to which color should be achieved, either small or large amounts are necessary of the color dispensing components and/or fireproof pigments and/or oxides and/or coloring and fluorescent metal oxides and/or organic or inorganic salts. Accordingly, the concentrations of the following are also to be in the loading body materials in order to create and to store the desired color: color dispensing components and/or fireproof pigments and/or oxides and/or coloring and fluorescent metal oxides and/or organic or inorganic salts.

Inventively the color pigment solution and/or the loading body solution memory and/or the loading body materials contain for implementation concentrations of all color dispensing and non-color dispensing components that are movable in the distribution management step.

During the distribution management step, the color dispensing solution is stably dissolved in order to prevent individual elements of the color pigment solution from being decomposed and/or pushed aside in a direction movement. For this purpose, pre-solutions made up for example of zircon (IV) oxide nitrate hydrate are appropriate.

Inventively, all known color-dispensing components contain organic and inorganic salts, which are applicable and which turn into an oxide during the desintering firing.

An inventive example of an embodiment is presented by a loading body solution device that maintains capillary pressure made of porous or spongy materials, which is also a loading body solution storage device, since the color dispensing components and/or fireproof pigments and/or oxides and/or coloring and fluorescent metal oxide and/or organic or inorganic salts are contained there. Thereby all further possibilities are well known to the person skilled in the art. See the list of nitrates.

Another inventive example of an embodiment is presented by a loading body that may possess all forms whereby the color dispensing components and/or fireproof pigments and/or oxides and/or coloring and fluorescent metal oxides and/or organic or inorganic salts contain at least one of the elements yttrium, iron, titanium, selenium, silver, indium, gold, chrome, copper, praseodymium, cobalt, nickel, manganese, erbium, cerium, or rare earth metals or mixtures of these, which are in the color dispensing components and/or non-color dispensing components added to the loading body material solution. The loading bodies may also be stored in airtight packaging under capillary pressure of the color pigment solution.

In addition, the layer strength of the loading body has a strength between 0.01 mm and 250 mm in and/or on the loading body material device that maintains the capillary pressure and are applied as loading body material memory and capillary strength reduction and filter. The layer strength varies in the area noted above from porosity and the concentration of the color pigment solution, depending on the diameter of the ceramic bodies. The color pigment solution can also be dried in the loading bodies in order then to rebuild the capillary pressure on the loading body material solution memory and/or the loading body material device that maintains the capillary pressure, which leads to the loading of the color pigment solution into the porosities.

It is also expeditious that the color pigment solution with the filling materials and color dispensing components and/or fireproof pigments and/or oxides and/or coloring and fluorescent metal oxides and/or organic or inorganic salts contained there are stored as loading body material. This is in order that the loading body materials have different geometric forms that are adaptable. This means also that color pigment solutions and the loading body materials at the same capillary pressure. Loading body materials may now be adapted on the ceramic blanks next to one another, over one another, or behind one another without the color pigment solutions getting mixed and in a way that the size or volume and selection of material of the loading body materials are also recordable as a desirable amount of color dispensing components.

Not all materials and/or components and non-color dispensing components or materials are added that can be used in the inventive method or in the inventive distribution management steps. Possibilities are made known to the person skilled in the art through the above embodiments.

BRIEF DESCRIPTION OF THE SEVERAL VIEWS OF THE DRAWING(S)

Other details, characteristics, combinations of characteristics, and effects based on the invention result from the following description of preferred, exemplary embodiments of the invention and from the drawings. These figures show:

FIG. 1 Flow diagram of the inventive method

Figure 2:
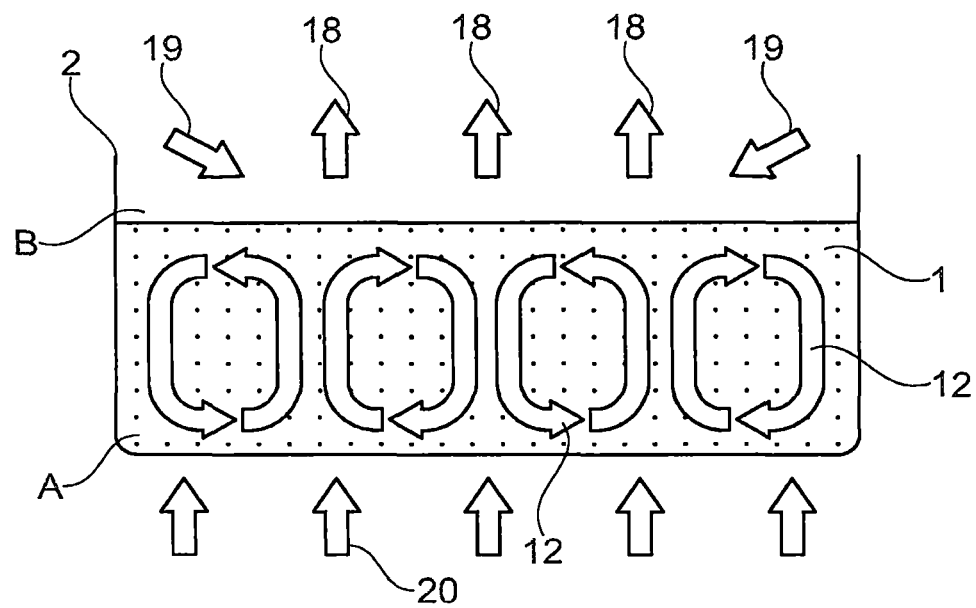
Figure 3:
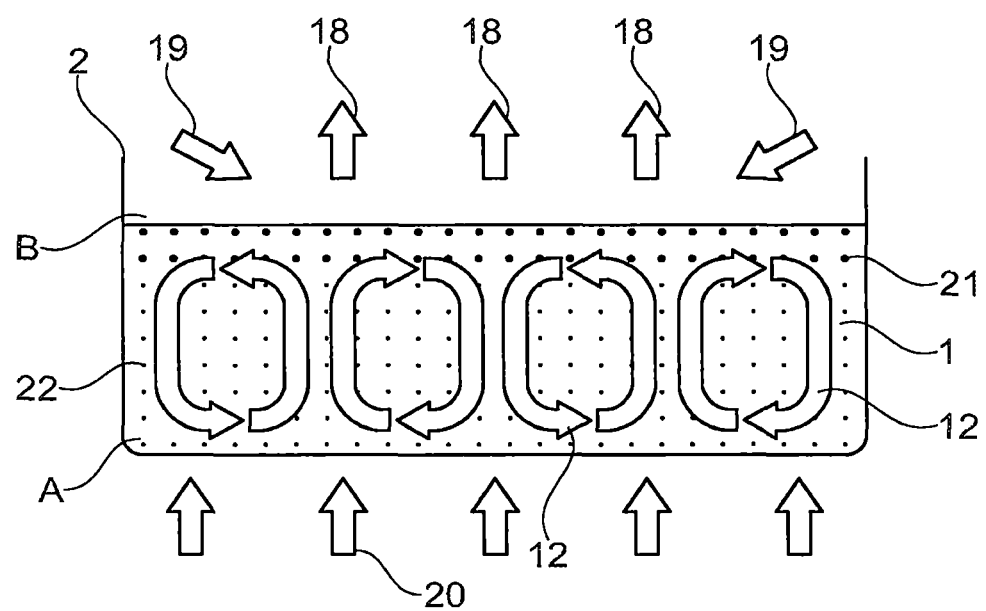
Figure 4:
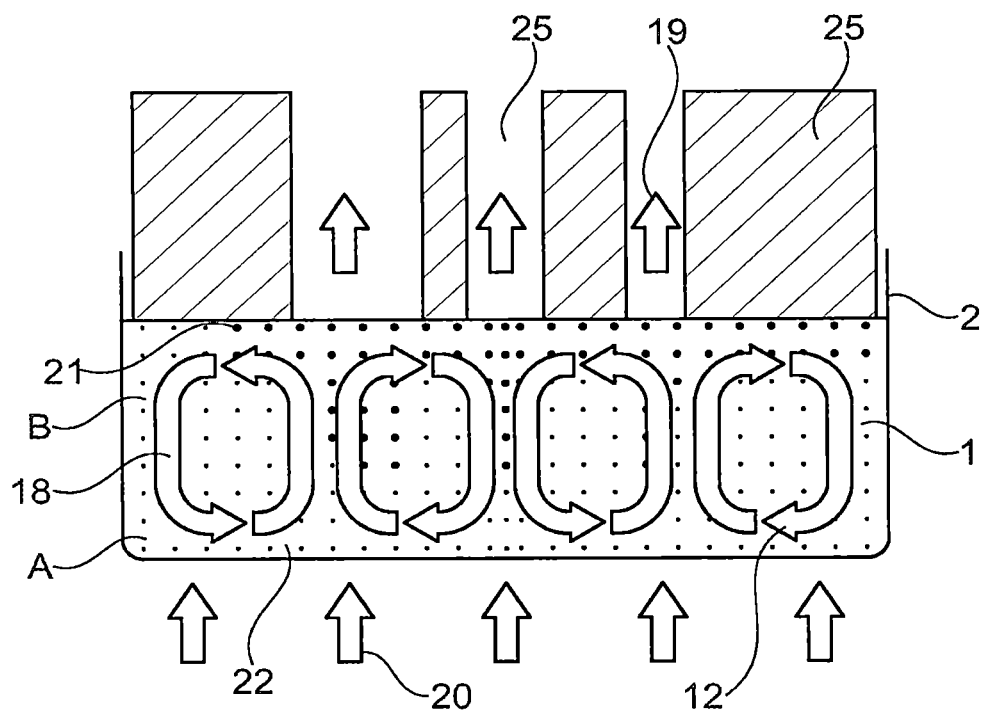
Figure 5:
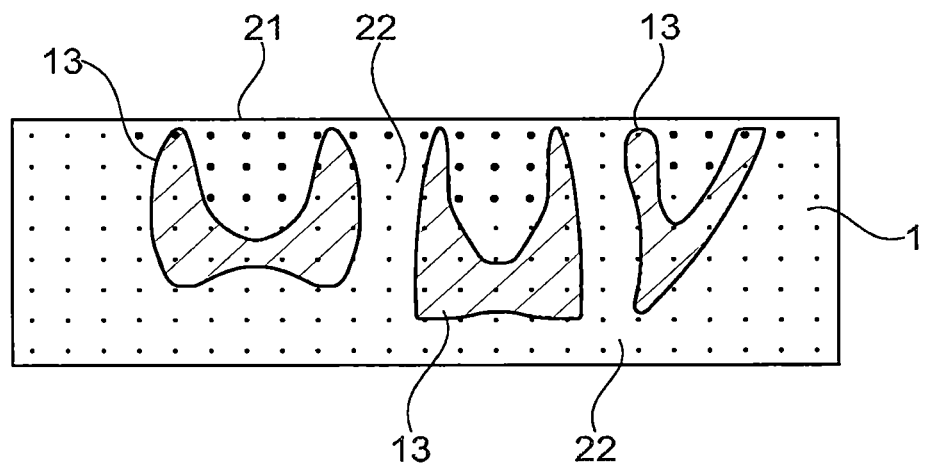
Figure 6:
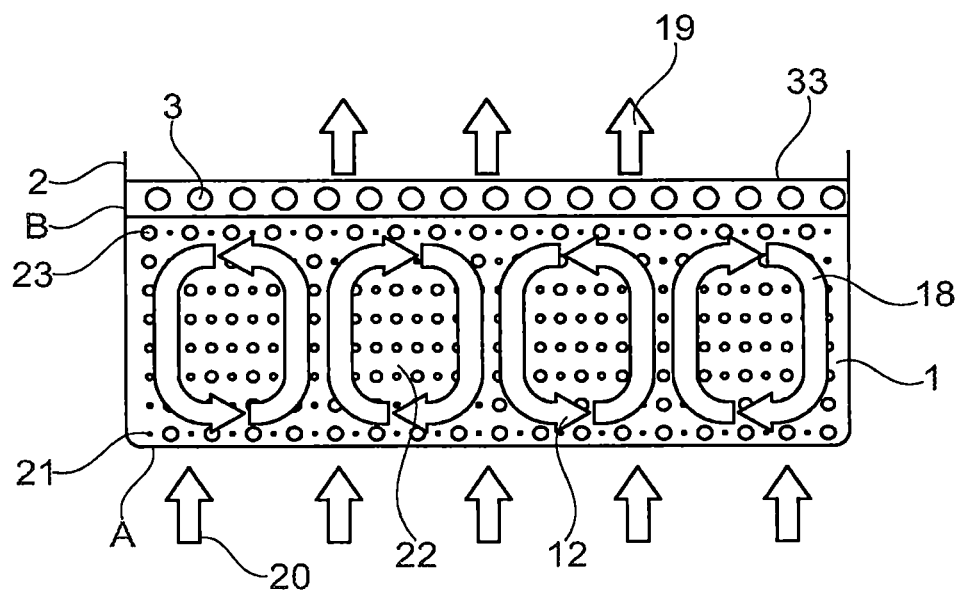
Figure 7:
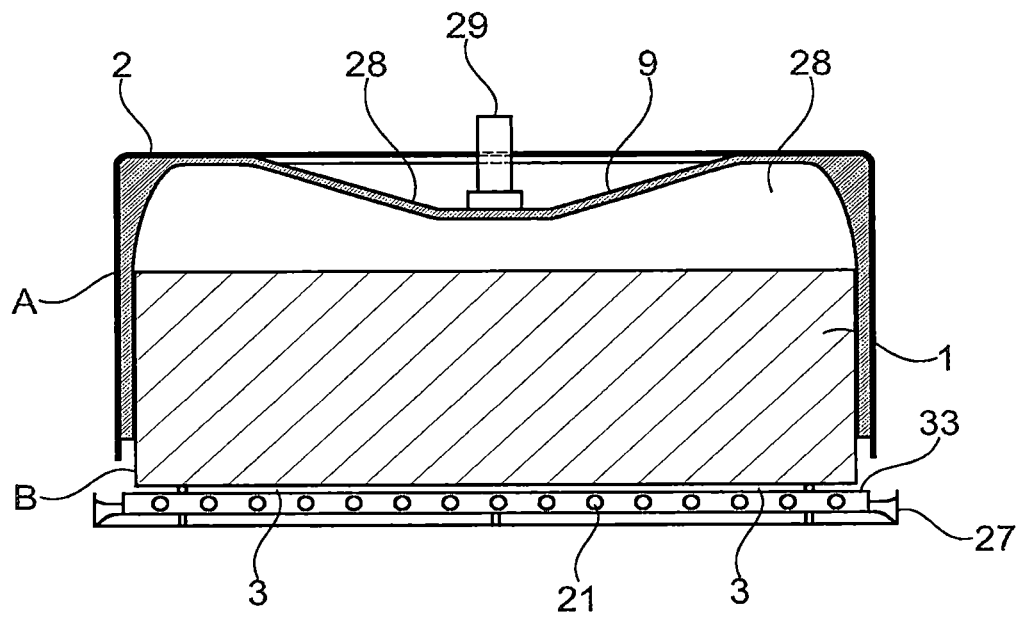
Figure 10:
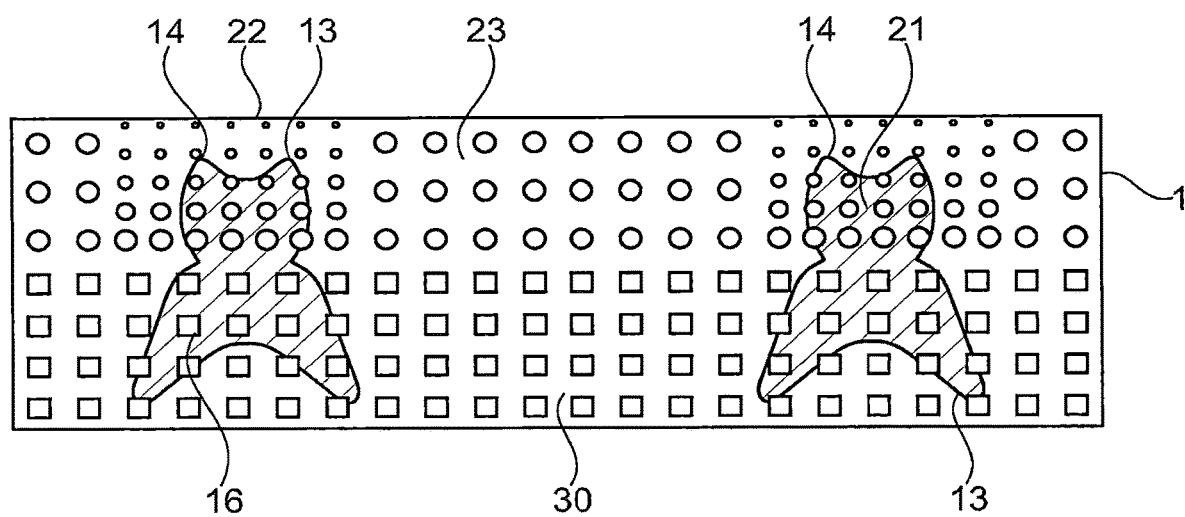
Figure 11:
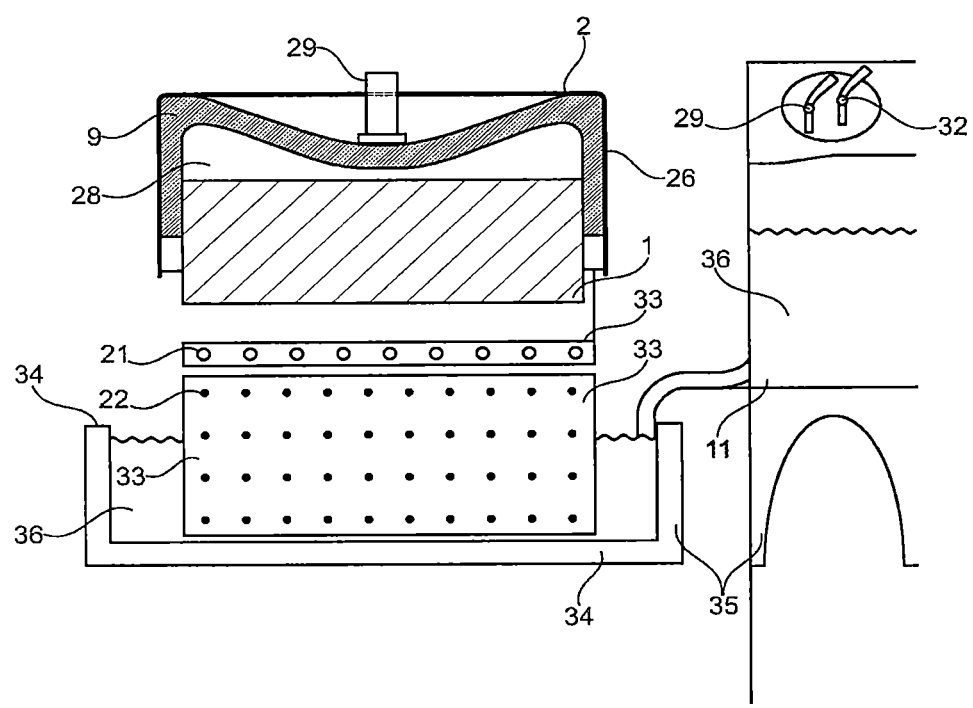
Figure 12:
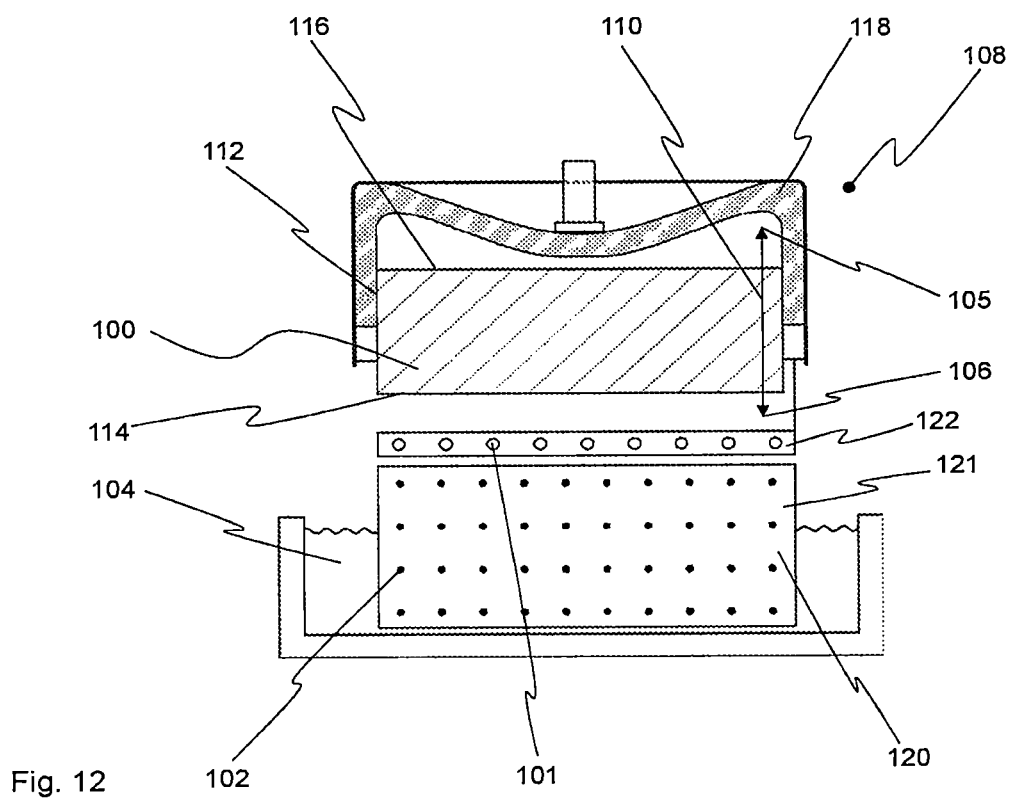

FIG. 2 Cross-section of a monochrome ceramic blank in the for example silicon housing FIG. 3 Cross-section of the polychromic ceramic blank in the for example silicon housing FIG. 4 Cross-section of the polychromic ceramic blank and spatially color concentration wave or spatially color concentration conical form in the silicon housing FIG. 5 Cross-section of the polychromic and spatially color concentration wave and spatially color concentration conical form with programmable CAD/CAM processing FIG. 6 The for example silicon housing concentration balance in the for example at least one loading body FIG. 7 The for example silicon housing for concentration balancing of the color concentration with at least one loading body solution memory cross-section with the loading body FIG. 8 Cross-section of the loading body FIG. 9 Cross-section of the stacked loading body FIG. 10 Prosthesis body—cross-section in the block FIG. 11 Cross-section—complete system of the for example silicon housing of the loading body material device for maintaining capillary pressure FIG. 12 A cross-section through a porous ceramic body, a distribution management device, and a loading body.

DETAILED DESCRIPTION OF THE INVENTION

FIG. 1 presents a flow diagram of the inventive measures.
A) Only porous and/or for pre-sintered and/or unbound and/or balance ceramics are prepared for the CAD/CAM processing.
B) The ceramic body is then laid in a sealing and insulating form that is as airtight as possible, for example in a silicone form housing. The for example silicon housing in all its sizes may have all parameters freely selectable and have no atmospheric pressure and/or can be constructed in such a way.

C) Then the loading body material device that maintains the capillary pressure loads the color pigment solution into the porosities of the porous ceramic blank through air-free loading. For this purpose, all loading body materials for or in the loading body material device that maintains the capillary pressure may have a balancing tank that is managed by capillary pressure in order to keep the capillary pressure constant.

D) Now the distribution management step of the color dispensing components into the porous ceramic in the for example silicon housing begins. The for example silicon housing contains or forms open and closed surfaces that are surrounded by a specific humidity in order to achieve the desired color dispensing with the movement direction of the color pigments.

E) Fluid removal to the end of the distribution management step.

F) Drying of the porous ceramic and/or heat handling for the creation of a nitrate oxide phase.

G) CAD/CAM processing

H) Heat treatment, fixing, and conversion of the color dispensing components into an oxide for dispensing color and the desintering into a sinter fire.

This means that the for example silicon housing encloses as densely as possible the side surfaces of the millable ceramic blank so that a ready-made flow may be adjusted as in a vessel. The color dispensing components that are inserted into the color dispensing solution may now be distributed equally or in the desired concentration flow. However, without sealing and/or insulating with the use of a form this is not manageable. Backups may result or there may be uncolored areas, as taught by EP 235 97 71. The enlargement or reduction of the for example silicon housing on the desired open surfaces allows the temperature and the surrounding variable humidity, multicolored spatially color concentration waves, or spatially color concentration conical forms to be set simply in the ceramic body, which can then form the natural buildup of the teeth. For example, EP 29 19 771 and/or Noritake give the teaching of milling out the ceramic block from dark to light into coatings and crowns with many cuts out of the right adjustment zone. In practice, however, there are crowns with many cuts and intensive color cores, where this is not possible in the block that is coated from dark to light because there is no dentine color coated in the zone with many cuts. Wolz teaches that any desired angle of the vertical and horizontal tooth axis is adjustable and movable and/or rotatable by 360° in the concentration of the 3 spatially color concentration waves or the spatially color concentration conical form. So for the first time there is a multiplicity of aesthetic possibilities that have programmable color zones available and that have a spatially color scheme.

The loading body materials may have various concentrations or may be managed one behind the other. These are brought into the desired positions of porosity of the ceramic blank through the loading body solution device that maintains the capillary pressure, by which the porosities can be completely managed. It turned out that at the same capillary pressure the color pigment solutions are held behind one another or next to one another without mixing them. In this way many colors are achievable that for the first time are distributed as desired in the for example silicon housing through an adjustable distribution management step of the color pigments.

Inventively a loading body material device is found on or under the for example silicon housing, which is filled with porous and/or spongy materials such as microfibers, sponges, cell material, etc. The loading body solution memory should be able to accept color pigment solutions in twice as many quantities as the prepared porous ceramic does. The loading body materials also store color dispensing and non-color dispensing components that lead to a stress balance of very high color concentrations in only one area of the ceramic blank at the time of the desintering fire, which then can be balanced on the facing side—e.g., FIG. 6. Moreover, the manufacture of a partial and/or total prosthetic blank, which has a tooth color, tooth arch, and a pink colored part that are adjustable in the distribution management step is achieved in the color distribution desired in the silicon housing. See FIG. 10.

FIG. 2 presents the cross-section of a monochrome porous ceramic blank, which is loaded with the loading body solution device that maintains the capillary pressure. Liquid is removed from the for example silicon housing. During the distribution management step, the porous ceramic blank is surrounded by the desired concentration in the for example silicon housing. The porous ceramic blank presents a ceramic filter without a silicon housing, in which clumps of concentrations are not desired in the infiltration, as DE 10 2008 026 980 teaches. In a for example silicon housing, from these clumps of concentrations a movement direction of the color pigments surprisingly can be managed for distribution into a porous ceramic blank. With the given complex loading solutions, spatially polychromics or monochrome colorings can also be loaded into the pre-prepared porous ceramic blanks. The various colors and chromates are known to the person skilled in the ceramic art and are also described in the literature that is presented. For example, a 7% zircon nitrate solution is implemented in order to achieve a chemically stable solution. This solution is mixed on the rolling block with about 20 rotations per minute for 24 hours. Subsequently an investigation occurs of the porosity volume of the desired pre-prepared ceramic blank. In the use of the available DD Bio zircon from the Dental Direkt Company Zx2 diameter 98 mm height 14 mm 3 yttrium TZP batch no. 50143002 weight 330 gr, a loading volume of 50 grams of loading material of the porosities was possible. This must be investigated anew for each manufacturer. Based on the investigation, various pigments of the color dispensing salts may now be added. 1-6 gr of erbium and 0.1 to 1 gr of iron should be mixed into 50 gr predissolved loading solution and mixed on the rolling block for 1-24 hours. The color settings depend on the porosity, purity of the basic materials, and desired color scheme of the chroma. The following amounts take priority in the manufacture of monochrome ceramic blanks. The color dispensing components are loaded onto surface A of the porous ceramic blank through the loading body material device that maintains the capillary pressure, and a loading under low capillary pressure is done in about 25 minutes with 50 gr of loading material onto the porous ceramic; it is then rotated by 180° if the for example silicon housing has no adjustable coverings. See FIG. 2. All the color components 4 flow to surface B of the porous ceramic blank after about 80%-90% fluid removal under 70% humidity on surface B; it is then again rotated by 180° if the convection housing has no adjustable coverings. The milling processing takes place after complete drying and/or working of the temperature into the nitrate oxide phase formation. In this way a homogeneous distribution of the concentration takes place since the fluid is removed before color concentrations can re-form. The data depend on the set viscosity of the color pigment solution and the porosity of the ceramic blank. The heat handling for the sintered ceramic object is typically to be performed under the following conditions. Depending on the ceramics that are used, atmospheric temperatures of approximately 700°-1600° are set. Air or vacuum or inert gas (nitrogen, argon gas), pressure: environmental pressure, duration: until a thickness of approximately 94% to 100% of the final density of the material is achieved.

FIG. 3 presents the cross-section of a polychromic porous ceramic blank in which a color dispensing concentration array from dark to light is manufactured. Surface B is processed with the loading body solution device that maintains the capillary pressure and the fluid is removed in the for example silicon form. The color dispensing components may be inserted under capillary pressure behind one another, over one another, or after one another in the loading body materials, depending on needs of the desired color. A simple capillary low-pressure loading with a color competent solution naturally also creates a distribution managed color scheme from dark to light of surface B, which is in contact with humidity of 30%-80%. It has also been discovered that for example at 50% humidity a stronger movement direction of the color pigments arises in the flow. There is thus darker and lighter, and at 80% 3 humidity there is for example less dark and less light movement direction of the color pigments from dark to light. The porous ceramic blank should be removed when there is no more motion of the liquids of the color components. The drying time depends on the porosity and size of the porous ceramic blank and the humidity, room temperature, and related desired color scheme.

FIG. 4 presents the cross-section of a polychromic ceramic blank that in addition has three-dimensional color zones. Surface B is processed with the loading body solution device that maintains the capillary pressure; in the convection housing with the most airtight surfaces possible and/or frames, pressure is placed on surface B and fluid is withdrawn. For the support of the loading body solution device that maintains capillary pressure, supplementary loading body materials may be loading body solution storage devices like FIG. 8 and FIG. 9, which support the loading body solution device that maintains capillary pressure. Surprisingly, the visible movement flow is so strong that a simple porous ceramic blank with the loading body solution device that maintains capillary pressure with a color dispensing component separates after the loading for example with adhesive tape stripes in order to create openings or covering surfaces. The distribution management step can be so strong that the porous ceramics are filled from all areas with the color dispensing components that flow to the open surfaces.

FIG. 5 presents the cross-section of a polychromic ceramic blank that in addition has three-dimensional color zones and is dried. The color scheme of the zones is presented graphically on a piece of software (13). The dental technician completely by himself or based on digital types of colors seeks the desired tooth color concentration scheme (21 (22). The CAD/CAM device then mills out the tooth replacement (13) from the desired zones of the ceramic blank (1).

FIG. 6 presents a cross-section of the porous ceramic blank that is already dried and that has a similar strong color concentration component (21) in surface area A. During final sintering, depending on the porosity and the manufacturing method of the ceramic blanks (1), there may be stresses within the final sintered ceramic body. With a known final sintering item, the porous ceramic or the ceramic blank is subject to high temperature handling, whereby material thickening is achieved and the porous spaces are filled. On the basis of different heating extension coefficients (WAK) of the various materials, for example of the ceramic blank and the infiltrated color pigments, the known stresses may occur through variable heat-related volume expansions. Creation of such stresses can be prevented in the manufacturing method of the porous ceramic blank. If there is a loading body with the corresponding non-color dispensing components with a capillary pressure loading, there may be simply an already dried porous ceramic blank as in FIG. 6. The concentration is calculated, and balanced with non-color dispensing components (23), such as zirconium (IV) oxynitrate hydrate and/or zircon compound II, III, IV and/or organic mineral zircon compounds. See table 1. Thus for example flowing nitrate complex areas (layer) with for example 75%, 50%, 25% of coloring nitrates and with similar proportions of balancing non-color dispensing nitrates are found in the porosities of the pre-prepared ceramic.

TABLE

| 3Y-TZP 12 mm thick takes place | | |
|---|---|---|
| | color nitrates | Balance with non-color dispensing nitrates |
| Flowing nitrate complex ~~coating~~ layer approximately 3 mm | 75% | 25% |
| Flowing nitrate complex ~~coating~~ layer approximately 3 mm | 50% | 50% |
| Flowing nitrate complex ~~coating~~ layer approximately 3 mm | 25% | 75% |
| Flowing nitrate complex ~~coating~~ layer approximately 3 mm | 0% | 100% |

FIG. 7 presents a cross-section of the loading body solution device that maintains capillary pressure in a for example silicon form housing. The porous ceramic blank is pressed in the for example silicon form housing and reduced with a valve or stamp (29) at atmospheric pressure. The porous ceramic blank is created as a capillary low-pressure loading on surface B on a dry and/or a loading body material standing under capillary pressure that is a loading body material memory storage device. The capillary spaces of a 14 mm high and 98 mm high diameter ceramic blank require approximately 50 gr of color pigment solution for filling the capillary space, which is achieved by a low-pressure capillary loading in the for example silicon housing in approximately 25 min. The time is however dependent on the color pigment solution concentration of the set viscosity of the capillary pressure, supported by conditions in the silicon housing and the type of material and size of the porosities.

FIG. 8 presents a cross-section of the loading body materials, which create color dispensing or non-color dispensing components in a low-pressure capillary loading in the porous ceramic, whereby the loading body materials stand under the same capillary pressure. The result is that there is no mixing of various color components (21) or non-color dispensing components (23). Thereby all possible color dispensings and tension balancings can be loaded into the porous ceramic by color pigment solution next to one another or behind one another or over one another. It is very important that the particular color dispensing form can be cut out, built, stamped, plotted etc. or manufactured into contours such as for example the jaw form, individual tooth forms, implants, abutment forms, or in a horizontal or vertical cross-section of the loading body materials. The loading body materials and capillary volumes of the concentration flow on the capillary volumes of the porous ceramic can be calculated.

FIG. 9 presents the cross-section of five loading body materials that are layered in order to create three-dimensional prosthetic bodies. For example, five loading body materials are laid over one another. For this purpose, 1.4 mm strong beer mats with a diameter of 104 mm are appropriate for storing these without problems over 10 g of color pigment solution and/or color dispensing components. This means that the necessary color pigment solution volumes are performed in five loading body materials without mixing in the porous ceramic blanks under low-pressure capillary loading on the loading body solution device that maintains capillary pressure. In the for example silicon housing liquid is now removed. The velocity of the removal of the fluid per 1.0 mm of the porous ceramic is 24 hours, depending how the color pigment solution is composed and manufactured and/or how the humidity atmosphere has been set from 50%-90%.

FIG. 10 presents a cross-section of a dry porous ceramic blank that has a polychromic spatially color scheme. The color scheme of the total prosthetic body is graphically presented by the software. The dental technician either himself or on the basis of digital color data determines the desired prosthetic body tooth color scheme. The CAD/CAM equipment then mills the desired prosthetic body with the corresponding color scheme out of the porous ceramic blank.

FIG. 11 presents the cross-section of the complete system with the for example silicon form housing and porous ceramic blanks (1) and exchangeable or layerable loading body materials (7) with possible color components under capillary pressure (21). Loading body solution device that maintains capillary pressure and the memory device from (7) (porous or foamy materials) with and/or without color dispensing components as a memory device with a possible balancing tank managed by capillary pressure, with a pressure valve under atmospheric pressure and/or a low-pressure application valve (29).

According to FIG. 12, the porous ceramic body 100 is fittable into a form 118, in particular a form-fitting silicon form, whereby a freely accessible surface 114 is available for loading with color pigments 101, 102, which are contained in a color pigment solution 104, onto a loading body 120 with two layers 121, 122. With regard to the freely accessible surface 114 and an insulated and/or sealed surface 116, an environmental parameter gradient 110 can be set between a parameter 105 within the form 118 and an environmental parameter 106 in an environment 108 by regulating the environmental parameter 106 and/or regulating parameter 105.

LIST OF REFERENCE NOTATION

1—Prepare a porous and/or sintered and/or unbound and/or bound ceramic
2—For example silicon form with inlaid porous ceramic blank
3—Loading of the porosities of the ceramic blank
4—Distribution step of the components
5—Removal of fluid until the end of the distribution management step in the for example silicon form
6—Drying of the porous ceramic blank
7—CAD/CAM processing
8—Inner surface of the replacement tooth and/or of the implant or implant prosthesis
9—Silicon
10—Valve
11—
12—Sign for distribution management step
13—Hatched images for the planned CAD/CAM processing
14—Prosthetic tooth
15—Pink color part
16—Possible storage in three-dimensional color space
17—Color components
18—Removal of fluid
19—Humidity
20—Temperature
21—Color dispensing component concentrations (large)
22—Color dispensing component concentrations (small)
23—Colorless components for example for concentration balancing large
24—Colorless components for example for concentration balancing small
25—For example silicon housing covering frame
26—
27—Vessel
28—Under atmospheric pressure area or without atmospheric pressure
29—Triggering valve under atmospheric pressure
30—Tooth color—pink gum color
31—Balancing tank managed by capillary pressure
32—Pressure setting valves
33—Loading bodies
34—Loading body solution device that maintains capillary pressure
35—Loading body material solution memory device
36—Color pigment solution
37—Stabilizers
a, b, c, d coloring with gradations from light to dark with and without color scheme
100—Porous ceramic
101, 102—color pigment
104—Color pigment solution
105—Parameter
106—Environmental parameter
108—Environment
110—Environmental parameter gradient
112—Insulated and/or sealed tile of a surface
114—Second freely accessible surface
116—First insulated and/or sealed surface
118—Form
120—Loading bodies
121, 122—Coding

The invention claimed is:

1. A method for manufacturing a polychromic or spatially polychromic or a monochrome colored ceramic body colored in this method, for management of a targeted distribution of color pigments (101, 102) within a porous ceramic (100) in a first step, which is a loading step (3c), the ceramic (100) is loaded with a color pigment solution (104), and in a second step, which is a distribution management step (4d), the distribution of the color pigments (101, 102) is managed inside the ceramic (100) by setting one or several environmental parameters (106) in an environment (108), characterized in that the distribution of the color pigments (101, 102) within the porous ceramic (100) is affected by a convection flow, whereby the direction of the flow and the velocity of the flow are managed by targeted creation of environmental parameter gradients (110) relative to various surfaces (114, 116) of the porous ceramic (100).

2. A method according to claim 1, characterized in that the direction of the convection flow and the velocity of the convection flow are managed through setting humidity differences or pressure differences or temperature differences relative to various surfaces (114, 116) of the porous ceramic (100).

3. A method according to claim 2, characterized in that the movement velocity of the color pigments (101, 102) or the flow velocity is managed by increasing or decreasing one or several environmental parameter gradients (110).

4. A method according to claim 2 characterized in that a movement direction of the color pigments (101, 102) or the direction of flow is managed by changing the direction of one or several environmental parameter gradients (110).

5. A method according to claim 1 characterized in that at least one surface (116) or at least a part of a surface (112) of the porous ceramic (100) is insulated or sealed during the loading step or during the distribution management step, and in that another surface (114) or at least another part of a surface of the porous ceramic (100) is freely accessible for loading or for management.

6. A method according to claim 1 characterized in that the solution contains water and zircon nitrate.

7. A method according to claim 1 characterized in that a loading of the porous ceramic (100) with color pigments 101, 102), using a loading body (120) whereby the loading body is treated with a solution and the color pigments contained in it (101, 102).

8. A method according to claim 7, characterized in that the porous ceramic (100) for loading with color pigments (101, 102) is laid on the loading body (120) with a freely accessible surface (114).

9. A method according to claim 7, characterized in that the loading body (120) comprises one or several layers (121, 122), whereby one or several layers (121, 122) contain equal color pigments (101, 102) or several layers (101, 102) contain various color pigments (101, 102) for creating a polychromic ceramic.

10. A method according to claim 7, whereby the loading of the porous ceramic (100) with color pigments 101, 102), using the loading body (120) is characterized in that the loading occurs out of a porous or spongy material and the loading body (120) is satiated with a solution and the color pigments contained in it (101, 102).

11. A method according to claim 1 characterized in that the porous ceramic (100) or the ceramic blank are treated with heat in a drying step after the distribution of the color pigments (101, 102), whereby the porous ceramic (100) or the ceramic blank is set for formation of an oxide phase at a temperature in a range between 80° C. and 1200° C.

12. A method according to claim 1 characterized in that during or after the distribution of the color pigments (101, 102) within the porous ceramic (100) a WAK [heat extension coefficient] balance is performed, whereby the porous ceramic (100) is at least partially loaded with a balancing material.

13. A method according to claim 1 characterized by the following steps:
Preparation of an essentially flat or plate shaped porous ceramic blank (100),
Provision of one or several surfaces (112, 116) of the ceramic blank (100) with insulation or sealing, whereby the ceramic blank is placed snugly inside a watertight and airtight form (118) so that at least one surface (114) of the ceramic blank is freely accessible,
Loading of the freely accessible surface (114) of the ceramic blank (100) color pigments (101, 102), whereby the color pigments (101, 102) are contained in a liquid solution,
Placement of the ceramic blank (100) within an environment (108) whose environmental parameters (106) are adjustable, whereby the freely accessible surface (114) of the ceramic blank (100) is in contact with the environment (108),
Management of the distribution of the color pigments (101, 102), within the ceramic blank (100), whereby at least one environmental parameter (108) is regulated for creation of an environmental parameter gradient (110) between the freely accessible surface (114) and the one or several insulated or sealed surfaces (112, 116) of the ceramic blank (100).

14. A method according to claim 1, characterized in that the ceramic body is a dental ceramic blank.

* * * * *